(12) United States Patent
Ottow et al.

(10) Patent No.: US 7,820,622 B2
(45) Date of Patent: Oct. 26, 2010

(54) TNF ANTAGONISTS

(75) Inventors: Helle Krogh Ottow, Mårslet (DK); Mette Munch, Egå (DK); Thor Las Holtet, Rønde (DK); Mikkel Holmen Andersen, Sporup (DK); Josephus Dirk Nieland, Aarhus C (DK)

(73) Assignee: Anaphore, Inc., La Jolla, CA (US)

( * ) Notice: Subject to any disclaimer, the term of this patent is extended or adjusted under 35 U.S.C. 154(b) by 590 days.

(21) Appl. No.: 11/719,942

(22) PCT Filed: Nov. 21, 2005

(86) PCT No.: PCT/DK2005/000742

§ 371 (c)(1), (2), (4) Date: Jul. 27, 2007

(87) PCT Pub. No.: WO2006/053568

PCT Pub. Date: May 26, 2006

(65) Prior Publication Data

US 2009/0155843 A1    Jun. 18, 2009

Related U.S. Application Data

(60) Provisional application No. 60/629,343, filed on Nov. 22, 2004.

(51) Int. Cl.
*A61K 38/00* (2006.01)
*C07H 21/02* (2006.01)
*C12N 15/00* (2006.01)
*C12N 1/20* (2006.01)

(52) U.S. Cl. .......... 514/12; 530/350; 435/69.1; 435/252.3; 435/320.1; 536/23.1

(58) Field of Classification Search ................ 530/350; 514/12; 435/69.1, 252.3, 320.1
See application file for complete search history.

(56) References Cited

FOREIGN PATENT DOCUMENTS

| WO | WO95/31540 A1 | 11/1995 |
|---|---|---|
| WO | WO98/56906 A | 12/1998 |
| WO | WO 02/48189 A2 | 6/2002 |
| WO | WO2004/039841 A2 | 5/2004 |

OTHER PUBLICATIONS

"ExPASy: the proteomics server for in-depth protein knowledge and analysis" Elizsabeth Gasteiger et al 3784-3788 Nucleic Acids Research, 2003, vol. 31, No. 13, DOI:10.1093/nar/gkg563.
Pennica D., et al (1984) Nature 312:724-729.
"Human tumour necrosis factor: precursor structure, expression and homology to lymphotoxin" Pennica D., et al Nature vol. 312 20/27, Dec. 1984, pp. 724-729.

*Primary Examiner*—Maryam Monshipouri
(74) *Attorney, Agent, or Firm*—McDonnell Boehnen Hulbert & Berghoff LLP

(57) ABSTRACT

TNF binding polypeptides based on human tetranectin C-type lectin like domains (CTLD) with improved binding characteristics and improved efficacy. The polypeptides comprise a TNF binding domain having the amino acid sequence KRWS-RYF (SEQ ID NO:1). Also provided are methods of preparing the polypeptides of the invention. The polypeptides may be used for the preparation of pharmaceutical compositions, and for treatment of a subject having a pathology mediated by TNF, such as treatment of rheumatoid arthritis.

27 Claims, 11 Drawing Sheets

Semi-quantitative clinical assessment based on arthritis scores (AS) of ankle joints on experimental Tg197 mice at 8 weeks of age.

SEQUENCE LISTING

```
<160> NUMBER OF SEQ ID NOS: 82

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Arg Trp Ser Arg Tyr Phe
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: variable amino acid
<220> FEATURE:
<221> NAME/KEY: MOD_RES
<222> LOCATION: (4)..(4)
<223> OTHER INFORMATION: variable amino acid

<400> SEQUENCE: 2

Pro Xaa Pro Xaa Asn
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hydrophilic amino acid
<220> FEATURE:
<221> NAME/KEY: MOD_RES
<222> LOCATION: (3)..(3)
<223> OTHER INFORMATION: variable amino acid
<220> FEATURE:
<221> NAME/KEY: MOD_RES
<222> LOCATION: (5)..(5)
<223> OTHER INFORMATION: variable amino acid
<220> FEATURE:
<221> NAME/KEY: MOD_RES
<222> LOCATION: (7)..(7)
<223> OTHER INFORMATION: hydrophobic amino acid
```

```
<400> SEQUENCE: 3

Xaa Pro Xaa Pro Xaa Asn Xaa
1               5

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Leu Pro Gln His Ala Gln Pro Asp Pro Ser Asn Trp
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu His Ser Ser Asp Ala Gln Pro Asp Pro Ser Asn Trp
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Glu Thr Thr Asp Ala Gln Pro Asp Pro Ser Asn Trp
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Arg Lys Glu Asp Ala Gln Pro Asp Pro Ser Asn Trp
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Leu Pro Gln His Ala Asn Pro Ser Pro Ser Asn Trp
1               5                   10

<210> SEQ ID NO 9
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Leu Pro Gln His Ala Asn Pro Asn Pro Ser Asn Trp
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Leu Pro Gln His Ala His Pro Glu Pro Ser Asn Trp
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Leu Pro Gln His Ala Ser Pro Ser Pro Ser Asn Trp
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Leu Glu Lys Asp Ala Gln Pro Asp Pro Ser Asn Trp
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Arg Lys Glu Asp Ala Gln Pro Asp Pro Ser Asn Trp
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Arg Thr Gln Asp Ala Gln Pro Asp Pro Ser Asn Trp
```

```
                               1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Arg Asn Arg Asp Ala Gln Pro Asp Pro Ser Asn Trp
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Arg Gln Arg Asp Ala Gln Pro Asp Pro Ser Asn Trp
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Arg Pro Glu Asp Ala Gln Pro Asp Pro Ser Asn Trp
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Arg Gln Glu Asp Ala Gln Pro Asp Pro Ser Asn Trp
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Arg Leu Arg Asp Ser Gln Pro Asp Pro Ser Asn Trp
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
                                peptide

<400> SEQUENCE: 20

Ala Ser Met Lys Asp Ala Gln Pro Asp Pro Ser Asn Trp
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Leu Pro Gln His Ala Asp Pro Ala Pro Ser Asn Trp
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Leu Pro Gln His Glu Gln Pro Glu Pro Ser Asn Trp
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Leu Ala Ser Asp Ala Gln Pro Asp Pro Ala Asn Trp
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Leu Ile Arg Asp Ala Gln Pro Asp Pro Ala Asn Trp
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Leu Leu Ser Asp Ala Gln Pro Asp Pro Val Asn Trp
1               5                   10

<210> SEQ ID NO 26
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Arg Arg Gln Asp Ala Gln Pro Asp Pro Ser Asn Trp
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Arg Leu Ala Asp Ala Gln Pro Asp Pro Phe Asn Trp
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Gly Ile Glu Trp Ala Gln Pro Asp Pro Thr Asn Phe
1               5                   10

<210> SEQ ID NO 29
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 29

Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
                20                  25                  30

Cys Ile Ser Arg Gly Gly Thr Leu Ser Thr Pro Gln Thr Gly Ser Glu
            35                  40                  45

Asn Asp Ala Leu Tyr Glu Tyr Leu Arg Gln Ser Val Gly Asn Glu Ala
        50                  55                  60

Glu Ile Trp Leu Gly Leu Asn Lys Arg Trp Ser Arg Tyr Phe Trp Val
65                  70                  75                  80

Asp Met Thr Gly Thr Arg Ile Ala Tyr Lys Asn Trp Glu Leu Pro Gln
                85                  90                  95

His Ala Gln Pro Asp Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
    130                 135
```

```
<210> SEQ ID NO 30
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 30

Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
            20                  25                  30

Cys Ile Ser Arg Gly Gly Thr Leu Ser Thr Pro Gln Thr Gly Ser Glu
        35                  40                  45

Asn Asp Ala Leu Tyr Glu Tyr Leu Arg Gln Ser Val Gly Asn Glu Ala
    50                  55                  60

Glu Ile Trp Leu Gly Leu Asn Lys Arg Trp Ser Arg Tyr Phe Trp Val
65                  70                  75                  80

Asp Met Thr Gly Thr Arg Ile Ala Tyr Lys Asn Trp Glu His Ser Ser
                85                  90                  95

Asp Ala Gln Pro Asp Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
    130                 135

<210> SEQ ID NO 31
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 31

Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
            20                  25                  30

Cys Ile Ser Arg Gly Gly Thr Leu Ser Thr Pro Gln Thr Gly Ser Glu
        35                  40                  45

Asn Asp Ala Leu Tyr Glu Tyr Leu Arg Gln Ser Val Gly Asn Glu Ala
    50                  55                  60

Glu Ile Trp Leu Gly Leu Asn Lys Arg Trp Ser Arg Tyr Phe Trp Val
65                  70                  75                  80

Asp Met Thr Gly Thr Arg Ile Ala Tyr Lys Asn Trp Glu Arg Thr Thr
                85                  90                  95

Asp Ala Gln Pro Asp Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
    130                 135

<210> SEQ ID NO 32
<211> LENGTH: 137
<212> TYPE: PRT
```

<213> ORGANISM: Artificial Sequence
<220> FEATURE:
<223> OTHER INFORMATION: Description of Artificial Sequence: Synthetic
      protein construct

<400> SEQUENCE: 32

Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
            20                  25                  30

Cys Ile Ser Arg Gly Gly Thr Leu Ser Thr Pro Gln Thr Gly Ser Glu
        35                  40                  45

Asn Asp Ala Leu Tyr Glu Tyr Leu Arg Gln Ser Val Gly Asn Glu Ala
    50                  55                  60

Glu Ile Trp Leu Gly Leu Asn Lys Arg Trp Ser Arg Tyr Phe Trp Val
65                  70                  75                  80

Asp Met Thr Gly Thr Arg Ile Ala Tyr Lys Asn Trp Gly Arg Lys Glu
                85                  90                  95

Asp Ala Gln Pro Asp Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
    130                 135

<210> SEQ ID NO 33
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 33

Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
            20                  25                  30

Cys Ile Ser Arg Gly Gly Thr Leu Ser Thr Pro Gln Thr Gly Ser Glu
        35                  40                  45

Asn Asp Ala Leu Tyr Glu Tyr Leu Arg Gln Ser Val Gly Asn Glu Ala
    50                  55                  60

Glu Ile Trp Leu Gly Leu Asn Lys Arg Trp Ser Arg Tyr Phe Trp Val
65                  70                  75                  80

Asp Met Thr Gly Thr Arg Ile Ala Tyr Lys Asn Trp Lys Leu Pro Gln
                85                  90                  95

His Ala Asn Pro Ser Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
    130                 135

<210> SEQ ID NO 34
<211> LENGTH: 137
<212> TYPE: PRT
<213> ORGANISM: Artificial Sequence
<220> FEATURE:
<223> OTHER INFORMATION: Description of Artificial Sequence: Synthetic -continued protein construct

<400> SEQUENCE: 34

Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
            20                  25                  30

Cys Ile Ser Arg Gly Gly Thr Leu Ser Thr Pro Gln Thr Gly Ser Glu
        35                  40                  45

Asn Asp Ala Leu Tyr Glu Tyr Leu Arg Gln Ser Val Gly Asn Glu Ala
    50                  55                  60

Glu Ile Trp Leu Gly Leu Asn Lys Arg Trp Ser Arg Tyr Phe Trp Val
65                  70                  75                  80

Asp Met Thr Gly Thr Arg Ile Ala Tyr Lys Asn Trp Leu Leu Pro Gln
                85                  90                  95

His Ala Asn Pro Asn Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
    130                 135

<210> SEQ ID NO 35
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 35

Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
            20                  25                  30

Cys Ile Ser Arg Gly Gly Thr Leu Ser Thr Pro Gln Thr Gly Ser Glu
        35                  40                  45

Asn Asp Ala Leu Tyr Glu Tyr Leu Arg Gln Ser Val Gly Asn Glu Ala
    50                  55                  60

Glu Ile Trp Leu Gly Leu Asn Lys Arg Trp Ser Arg Tyr Phe Trp Val
65                  70                  75                  80

Asp Met Thr Gly Thr Arg Ile Ala Tyr Lys Asn Trp Lys Leu Pro Gln
                85                  90                  95

His Ala His Pro Glu Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
    130                 135

<210> SEQ ID NO 36
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 36

Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
            20                  25                  30

Cys Ile Ser Arg Gly Gly Thr Leu Ser Thr Pro Gln Thr Gly Ser Glu
        35                  40                  45

Asn Asp Ala Leu Tyr Glu Tyr Leu Arg Gln Ser Val Gly Asn Glu Ala
    50                  55                  60

Glu Ile Trp Leu Gly Leu Asn Lys Arg Trp Ser Arg Tyr Phe Trp Val
65                  70                  75                  80

Asp Met Thr Gly Thr Arg Ile Ala Tyr Lys Asn Trp Ala Leu Pro Gln
                85                  90                  95

His Ala Ser Pro Ser Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
    130                 135

<210> SEQ ID NO 37
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 37

Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
            20                  25                  30

Cys Ile Ser Arg Gly Gly Thr Leu Ser Thr Pro Gln Thr Gly Ser Glu
        35                  40                  45

Asn Asp Ala Leu Tyr Glu Tyr Leu Arg Gln Ser Val Gly Asn Glu Ala
    50                  55                  60

Glu Ile Trp Leu Gly Leu Asn Lys Arg Trp Ser Arg Tyr Phe Trp Val
65                  70                  75                  80

Asp Met Thr Gly Thr Arg Ile Ala Tyr Lys Asn Trp Met Leu Glu Lys
                85                  90                  95

Asp Ala Gln Pro Asp Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
    130                 135

<210> SEQ ID NO 38
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 38

Ala Leu Gln Thr Val Cys Leu Lys Gly Thr Lys Val His Met Lys Cys
1               5                   10                  15

```
Phe Leu Ala Phe Thr Gln Thr Lys Thr Phe His Glu Ala Ser Glu Asp
            20                  25                  30

Cys Ile Ser Arg Gly Gly Thr Leu Ser Thr Pro Gln Thr Gly Ser Glu
            35                  40                  45

Asn Asp Ala Leu Tyr Glu Tyr Leu Arg Gln Ser Val Gly Asn Glu Ala
            50                  55                  60

Glu Ile Trp Leu Gly Leu Asn Lys Arg Trp Ser Arg Tyr Phe Trp Val
 65                  70                  75                  80

Asp Met Thr Gly Thr Arg Ile Ala Tyr Lys Asn Trp Gly Arg Lys Glu
                 85                  90                  95

Asp Ala Gln Pro Asp Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
            115                 120                 125

Pro Tyr Ile Cys Gln Phe Gly Ile Val
            130                 135

<210> SEQ ID NO 39
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 39

Ala Leu Gln Thr Val Cys Leu Lys Gly Thr Lys Val His Met Lys Cys
 1               5                  10                  15

Phe Leu Ala Phe Thr Gln Thr Lys Thr Phe His Glu Ala Ser Glu Asp
            20                  25                  30

Cys Ile Ser Arg Gly Gly Thr Leu Ser Thr Pro Gln Thr Gly Ser Glu
            35                  40                  45

Asn Asp Ala Leu Tyr Glu Tyr Leu Arg Gln Ser Val Gly Asn Glu Ala
            50                  55                  60

Glu Ile Trp Leu Gly Leu Asn Lys Arg Trp Ser Arg Tyr Phe Trp Val
 65                  70                  75                  80

Asp Met Thr Gly Thr Arg Ile Ala Tyr Lys Asn Trp Ala Arg Thr Gln
                 85                  90                  95

Asp Ala Gln Pro Asp Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
            115                 120                 125

Pro Tyr Ile Cys Gln Phe Gly Ile Val
            130                 135

<210> SEQ ID NO 40
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 40

Ala Leu Gln Thr Val Cys Leu Lys Gly Thr Lys Val His Met Lys Cys
 1               5                  10                  15

Phe Leu Ala Phe Thr Gln Thr Lys Thr Phe His Glu Ala Ser Glu Asp
            20                  25                  30
```

Cys Ile Ser Arg Gly Gly Thr Leu Ser Thr Pro Gln Thr Gly Ser Glu
            35                  40                  45

Asn Asp Ala Leu Tyr Glu Tyr Leu Arg Gln Ser Val Gly Asn Glu Ala
        50                  55                  60

Glu Ile Trp Leu Gly Leu Asn Lys Arg Trp Ser Arg Tyr Phe Trp Val
65                  70                  75                  80

Asp Met Thr Gly Thr Arg Ile Ala Tyr Lys Asn Trp Glu Arg Asn Arg
                85                  90                  95

Asp Ala Gln Pro Asp Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
        130                 135

<210> SEQ ID NO 41
<211> LENGTH: 137
<212> TYPE: PRT
<213> ORGANISM: Artificial Sequence
<220> FEATURE:
<223> OTHER INFORMATION: Description of Artificial Sequence: Synthetic
    protein construct

<400> SEQUENCE: 41

Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
                20                  25                  30

Cys Ile Ser Arg Gly Gly Thr Leu Ser Thr Pro Gln Thr Gly Ser Glu
            35                  40                  45

Asn Asp Ala Leu Tyr Glu Tyr Leu Arg Gln Ser Val Gly Asn Glu Ala
        50                  55                  60

Glu Ile Trp Leu Gly Leu Asn Lys Arg Trp Ser Arg Tyr Phe Trp Val
65                  70                  75                  80

Asp Met Thr Gly Thr Arg Ile Ala Tyr Lys Asn Trp Val Arg Gln Arg
                85                  90                  95

Asp Ala Gln Pro Asp Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
        130                 135

<210> SEQ ID NO 42
<211> LENGTH: 137
<212> TYPE: PRT
<213> ORGANISM: Artificial Sequence
<220> FEATURE:
<223> OTHER INFORMATION: Description of Artificial Sequence: Synthetic
    protein construct

<400> SEQUENCE: 42

Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
                20                  25                  30

Cys Ile Ser Arg Gly Gly Thr Leu Ser Thr Pro Gln Thr Gly Ser Glu
            35                  40                  45

```
Asn Asp Ala Leu Tyr Glu Tyr Leu Arg Gln Ser Val Gly Asn Glu Ala
         50                  55                  60

Glu Ile Trp Leu Gly Leu Asn Lys Arg Trp Ser Arg Tyr Phe Trp Val
 65                  70                  75                  80

Asp Met Thr Gly Thr Arg Ile Ala Tyr Lys Asn Trp Glu Arg Pro Glu
                 85                  90                  95

Asp Ala Gln Pro Asp Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
    130                 135

<210> SEQ ID NO 43
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 43

Ala Leu Gln Thr Val Cys Leu Lys Gly Thr Lys Val His Met Lys Cys
 1               5                  10                  15

Phe Leu Ala Phe Thr Gln Thr Lys Thr Phe His Glu Ala Ser Glu Asp
                20                  25                  30

Cys Ile Ser Arg Gly Gly Thr Leu Ser Thr Pro Gln Thr Gly Ser Glu
            35                  40                  45

Asn Asp Ala Leu Tyr Glu Tyr Leu Arg Gln Ser Val Gly Asn Glu Ala
         50                  55                  60

Glu Ile Trp Leu Gly Leu Asn Lys Arg Trp Ser Arg Tyr Phe Trp Val
 65                  70                  75                  80

Asp Met Thr Gly Thr Arg Ile Ala Tyr Lys Asn Trp Ser Arg Gln Glu
                 85                  90                  95

Asp Ala Gln Pro Asp Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
    130                 135

<210> SEQ ID NO 44
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 44

Ala Leu Gln Thr Val Cys Leu Lys Gly Thr Lys Val His Met Lys Cys
 1               5                  10                  15

Phe Leu Ala Phe Thr Gln Thr Lys Thr Phe His Glu Ala Ser Glu Asp
                20                  25                  30

Cys Ile Ser Arg Gly Gly Thr Leu Ser Thr Pro Gln Thr Gly Ser Glu
            35                  40                  45

Asn Asp Ala Leu Tyr Glu Tyr Leu Arg Gln Ser Val Gly Asn Glu Ala
         50                  55                  60
```

```
Glu Ile Trp Leu Gly Leu Asn Lys Arg Trp Ser Arg Tyr Phe Trp Val
 65                  70                  75                  80

Asp Met Thr Gly Thr Arg Ile Ala Tyr Lys Asn Trp Glu Arg Leu Arg
                 85                  90                  95

Asp Ser Gln Pro Asp Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
    130                 135

<210> SEQ ID NO 45
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 45

Glu Pro Pro Thr Gln Lys Pro Lys Lys Ile Val Asn Ala Lys Lys Asp
  1               5                  10                  15

Val Val Asn Thr Lys Met Phe Glu Glu Leu Lys Ser Arg Leu Asp Thr
                 20                  25                  30

Leu Ala Gln Glu Val Ala Leu Leu Lys Glu Gln Gln Ala Leu Gln Thr
            35                  40                  45

Val Cys Leu Lys Gly Thr Lys Val His Met Lys Cys Phe Leu Ala Phe
 50                  55                  60

Thr Gln Thr Lys Thr Phe His Glu Ala Ser Glu Asp Cys Ile Ser Arg
 65                  70                  75                  80

Gly Gly Thr Leu Ser Thr Pro Gln Thr Gly Ser Glu Asn Asp Ala Leu
                 85                  90                  95

Tyr Glu Tyr Leu Arg Gln Ser Val Gly Asn Glu Ala Glu Ile Trp Leu
            100                 105                 110

Gly Leu Asn Lys Arg Trp Ser Arg Tyr Phe Trp Val Asp Met Thr Gly
        115                 120                 125

Thr Arg Ile Ala Tyr Lys Asn Trp Ala Ser Met Lys Asp Ala Gln Pro
130                 135                 140

Asp Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 46
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 46

Ala Leu Gln Thr Val Cys Leu Lys Gly Thr Lys Val His Met Lys Cys
  1               5                  10                  15

Phe Leu Ala Phe Thr Gln Thr Lys Thr Phe His Glu Ala Ser Glu Asp
                 20                  25                  30
```

```
Cys Ile Ser Arg Gly Gly Thr Leu Ser Thr Pro Gln Thr Gly Ser Glu
            35                  40                  45

Asn Asp Ala Leu Tyr Glu Tyr Leu Arg Gln Ser Val Gly Asn Glu Ala
        50                  55                  60

Glu Ile Trp Leu Gly Leu Asn Lys Arg Trp Ser Arg Tyr Phe Trp Val
65                  70                  75                  80

Asp Met Thr Gly Thr Arg Ile Ala Tyr Lys Asn Trp Gln Leu Pro Gln
                85                  90                  95

His Ala Asp Pro Ala Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
        130                 135
```

<210> SEQ ID NO 47
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 47

```
Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
            20                  25                  30

Cys Ile Ser Arg Gly Gly Thr Leu Ser Thr Pro Gln Thr Gly Ser Glu
        35                  40                  45

Asn Asp Ala Leu Tyr Glu Tyr Leu Arg Gln Ser Val Gly Asn Glu Ala
    50                  55                  60

Glu Ile Trp Leu Gly Leu Asn Lys Arg Trp Ser Arg Tyr Phe Trp Val
65                  70                  75                  80

Asp Met Thr Gly Thr Arg Ile Ala Tyr Lys Asn Trp Leu Leu Pro Gln
                85                  90                  95

His Glu Gln Pro Glu Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
        130                 135
```

<210> SEQ ID NO 48
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 48

```
Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
            20                  25                  30

Cys Ile Ser Arg Gly Gly Thr Leu Ser Thr Pro Gln Thr Gly Ser Glu
        35                  40                  45
```

```
Asn Asp Ala Leu Tyr Glu Tyr Leu Arg Gln Ser Val Gly Asn Glu Ala
         50                  55                  60

Glu Ile Trp Leu Gly Leu Asn Lys Arg Trp Ser Arg Tyr Phe Trp Val
 65                  70                  75                  80

Asp Met Thr Gly Thr Arg Ile Ala Tyr Lys Asn Trp Glu Leu Ala Ser
                 85                  90                  95

Asp Ala Gln Pro Asp Pro Ala Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
    130                 135

<210> SEQ ID NO 49
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 49

Ala Leu Gln Thr Val Cys Leu Lys Gly Thr Lys Val His Met Lys Cys
 1               5                  10                  15

Phe Leu Ala Phe Thr Gln Thr Lys Thr Phe His Glu Ala Ser Glu Asp
                 20                  25                  30

Cys Ile Ser Arg Gly Gly Thr Leu Ser Thr Pro Gln Thr Gly Ser Glu
             35                  40                  45

Asn Asp Ala Leu Tyr Glu Tyr Leu Arg Gln Ser Val Gly Asn Glu Ala
         50                  55                  60

Glu Ile Trp Leu Gly Leu Asn Lys Arg Trp Ser Arg Tyr Phe Trp Val
 65                  70                  75                  80

Asp Met Thr Gly Thr Arg Ile Ala Tyr Lys Asn Trp Glu Leu Ile Arg
                 85                  90                  95

Asp Ala Gln Pro Asp Pro Ala Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
    130                 135

<210> SEQ ID NO 50
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 50

Ala Leu Gln Thr Val Cys Leu Lys Gly Thr Lys Val His Met Lys Cys
 1               5                  10                  15

Phe Leu Ala Phe Thr Gln Thr Lys Thr Phe His Glu Ala Ser Glu Asp
                 20                  25                  30

Cys Ile Ser Arg Gly Gly Thr Leu Ser Thr Pro Gln Thr Gly Ser Glu
             35                  40                  45

Asn Asp Ala Leu Tyr Glu Tyr Leu Arg Gln Ser Val Gly Asn Glu Ala
         50                  55                  60
```

```
Glu Ile Trp Leu Gly Leu Asn Lys Arg Trp Ser Arg Tyr Phe Trp Val
65                  70                  75                  80

Asp Met Thr Gly Thr Arg Ile Ala Tyr Lys Asn Trp Glu Leu Leu Ser
                85                  90                  95

Asp Ala Gln Pro Asp Pro Val Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
    130                 135

<210> SEQ ID NO 51
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 51

Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
                20                  25                  30

Cys Ile Ser Arg Gly Gly Thr Leu Ser Thr Pro Gln Thr Gly Ser Glu
            35                  40                  45

Asn Asp Ala Leu Tyr Glu Tyr Leu Arg Gln Ser Val Gly Asn Glu Ala
        50                  55                  60

Glu Ile Trp Leu Gly Leu Asn Lys Arg Trp Ser Arg Tyr Phe Trp Val
65                  70                  75                  80

Asp Met Thr Gly Thr Arg Ile Ala Tyr Lys Asn Trp Glu Arg Arg Gln
                85                  90                  95

Asp Ala Gln Pro Asp Pro Ser Asn Trp Glu Asn Cys Ala Val Leu Ser
            100                 105                 110

Gly Ala Ala Asn Gly Lys Trp Phe Gly Lys Arg Cys Arg Asp Gln Leu
        115                 120                 125

Pro Tyr Ile Cys Gln Phe Gly Ile Val
    130                 135

<210> SEQ ID NO 52
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 52

Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
                20                  25                  30

Cys Ile Ser Arg Gly Gly Thr Leu Ser Thr Pro Gln Thr Gly Ser Glu
            35                  40                  45

Asn Asp Ala Leu Tyr Glu Tyr Leu Arg Gln Ser Val Gly Asn Glu Ala
        50                  55                  60

Glu Ile Trp Leu Gly Leu Asn Lys Arg Trp Ser Arg Tyr Phe Trp Val
65                  70                  75                  80
```

Asp Met Thr Gly Thr Arg Ile Ala Tyr Lys Asn Trp Glu Arg Leu Ala
                85                  90                  95

Asp Ala Gln Pro Asp Pro Phe Asn Trp Glu Asn Cys Ala Val Leu Ser
            100                 105                 110

Gly Ala Ala Asn Gly Lys Trp Phe Gly Lys Arg Cys Arg Asp Gln Leu
            115                 120                 125

Pro Tyr Ile Cys Gln Phe Gly Ile Val
            130                 135

<210> SEQ ID NO 53
<211> LENGTH: 137
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 53

Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
            20                  25                  30

Cys Ile Ser Arg Gly Gly Thr Leu Ser Thr Pro Gln Thr Gly Ser Glu
        35                  40                  45

Asn Asp Ala Leu Tyr Glu Tyr Leu Arg Gln Ser Val Gly Asn Glu Ala
    50                  55                  60

Glu Ile Trp Leu Gly Leu Asn Lys Arg Trp Ser Arg Tyr Phe Trp Val
65                  70                  75                  80

Asp Met Thr Gly Thr Arg Ile Ala Tyr Lys Asn Trp Glu Gly Ile Glu
                85                  90                  95

Trp Ala Gln Pro Asp Pro Thr Asn Phe Glu Asn Cys Ala Val Leu Ser
            100                 105                 110

Gly Ala Ala Asn Gly Lys Trp Phe Gly Lys Arg Cys Arg Asp Gln Leu
            115                 120                 125

Pro Tyr Ile Cys Gln Phe Gly Ile Val
            130                 135

<210> SEQ ID NO 54
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 54

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
            35                  40                  45

Val Cys Leu Lys Gly Thr Lys Val His Met Lys Cys Phe Leu Ala Phe
        50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
                100                 105                 110

Gly Leu Asn Lys Arg Trp Ser Arg Tyr Phe Trp Val Asp Met Thr Gly
            115                 120                 125

Thr Arg Ile Ala Tyr Lys Asn Trp Glu Leu Pro Gln His Ala Gln Pro
        130                 135                 140

Asp Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 55
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 55

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
                100                 105                 110

Gly Leu Asn Lys Arg Trp Ser Arg Tyr Phe Trp Val Asp Met Thr Gly
            115                 120                 125

Thr Arg Ile Ala Tyr Lys Asn Trp Glu His Ser Ser Asp Ala Gln Pro
        130                 135                 140

Asp Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 56
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 56

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
            100                 105                 110

Gly Leu Asn Lys Arg Trp Ser Arg Tyr Phe Trp Val Asp Met Thr Gly
        115                 120                 125

Thr Arg Ile Ala Tyr Lys Asn Trp Glu Arg Thr Thr Asp Ala Gln Pro
    130                 135                 140

Asp Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 57
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 57

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
            100                 105                 110

Gly Leu Asn Lys Arg Trp Ser Arg Tyr Phe Trp Val Asp Met Thr Gly
        115                 120                 125

Thr Arg Ile Ala Tyr Lys Asn Trp Gly Arg Lys Glu Asp Ala Gln Pro
    130                 135                 140

Asp Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val

<210> SEQ ID NO 58
<211> LENGTH: 181
<212> TYPE: PRT
<213> ORGANISM: Artificial Sequence
<220> FEATURE:
<223> OTHER INFORMATION: Description of Artificial Sequence: Synthetic protein construct

<400> SEQUENCE: 58

```
Glu Pro Pro Thr Gln Lys Pro Lys Lys Ile Val Asn Ala Lys Lys Asp
1               5                   10                  15
Val Val Asn Thr Lys Met Phe Glu Glu Leu Lys Ser Arg Leu Asp Thr
            20                  25                  30
Leu Ala Gln Glu Val Ala Leu Leu Lys Glu Gln Gln Ala Leu Gln Thr
        35                  40                  45
Val Cys Leu Lys Gly Thr Lys Val His Met Lys Cys Phe Leu Ala Phe
    50                  55                  60
Thr Gln Thr Lys Thr Phe His Glu Ala Ser Glu Asp Cys Ile Ser Arg
65                  70                  75                  80
Gly Gly Thr Leu Ser Thr Pro Gln Thr Gly Ser Glu Asn Asp Ala Leu
                85                  90                  95
Tyr Glu Tyr Leu Arg Gln Ser Val Gly Asn Glu Ala Glu Ile Trp Leu
            100                 105                 110
Gly Leu Asn Lys Arg Trp Ser Arg Tyr Phe Trp Val Asp Met Thr Gly
        115                 120                 125
Thr Arg Ile Ala Tyr Lys Asn Trp Lys Leu Pro Gln His Ala Asn Pro
    130                 135                 140
Ser Pro Ser Asn Trp Glu Asn Cys Ala Val Leu Ser Gly Ala Ala Asn
145                 150                 155                 160
Gly Lys Trp Phe Gly Lys Arg Cys Arg Asp Gln Leu Pro Tyr Ile Cys
                165                 170                 175
Gln Phe Gly Ile Val
            180
```

<210> SEQ ID NO 59
<211> LENGTH: 181
<212> TYPE: PRT
<213> ORGANISM: Artificial Sequence
<220> FEATURE:
<223> OTHER INFORMATION: Description of Artificial Sequence: Synthetic protein construct

<400> SEQUENCE: 59

```
Glu Pro Pro Thr Gln Lys Pro Lys Lys Ile Val Asn Ala Lys Lys Asp
1               5                   10                  15
Val Val Asn Thr Lys Met Phe Glu Glu Leu Lys Ser Arg Leu Asp Thr
            20                  25                  30
Leu Ala Gln Glu Val Ala Leu Leu Lys Glu Gln Gln Ala Leu Gln Thr
        35                  40                  45
Val Cys Leu Lys Gly Thr Lys Val His Met Lys Cys Phe Leu Ala Phe
    50                  55                  60
Thr Gln Thr Lys Thr Phe His Glu Ala Ser Glu Asp Cys Ile Ser Arg
65                  70                  75                  80
Gly Gly Thr Leu Ser Thr Pro Gln Thr Gly Ser Glu Asn Asp Ala Leu
                85                  90                  95
Tyr Glu Tyr Leu Arg Gln Ser Val Gly Asn Glu Ala Glu Ile Trp Leu
```

```
                    100                 105                 110
Gly Leu Asn Lys Arg Trp Ser Arg Tyr Phe Trp Val Asp Met Thr Gly
            115                 120                 125

Thr Arg Ile Ala Tyr Lys Asn Trp Leu Leu Pro Gln His Ala Asn Pro
        130                 135                 140

Asn Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 60
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 60

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
            100                 105                 110

Gly Leu Asn Lys Arg Trp Ser Arg Tyr Phe Trp Val Asp Met Thr Gly
        115                 120                 125

Thr Arg Ile Ala Tyr Lys Asn Trp Lys Leu Pro Gln His Ala His Pro
    130                 135                 140

Glu Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 61
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 61

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
```

-continued

```
                  20                  25                  30

Leu Ala Gln Glu Val Ala Leu Leu Lys Glu Gln Gln Ala Leu Gln Thr
            35                  40                  45

Val Cys Leu Lys Gly Thr Lys Val His Met Lys Cys Phe Leu Ala Phe
 50                  55                  60

Thr Gln Thr Lys Thr Phe His Glu Ala Ser Glu Asp Cys Ile Ser Arg
 65                  70                  75                  80

Gly Gly Thr Leu Ser Thr Pro Gln Thr Gly Ser Glu Asn Asp Ala Leu
                 85                  90                  95

Tyr Glu Tyr Leu Arg Gln Ser Val Gly Asn Glu Ala Glu Ile Trp Leu
                100                 105                 110

Gly Leu Asn Lys Arg Trp Ser Arg Tyr Phe Trp Val Asp Met Thr Gly
                115                 120                 125

Thr Arg Ile Ala Tyr Lys Asn Trp Ala Leu Pro Gln His Ala Ser Pro
130                 135                 140

Ser Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
                180

<210> SEQ ID NO 62
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 62

Glu Pro Pro Thr Gln Lys Pro Lys Lys Ile Val Asn Ala Lys Lys Asp
 1               5                  10                  15

Val Val Asn Thr Lys Met Phe Glu Glu Leu Lys Ser Arg Leu Asp Thr
                20                  25                  30

Leu Ala Gln Glu Val Ala Leu Leu Lys Glu Gln Gln Ala Leu Gln Thr
            35                  40                  45

Val Cys Leu Lys Gly Thr Lys Val His Met Lys Cys Phe Leu Ala Phe
 50                  55                  60

Thr Gln Thr Lys Thr Phe His Glu Ala Ser Glu Asp Cys Ile Ser Arg
 65                  70                  75                  80

Gly Gly Thr Leu Ser Thr Pro Gln Thr Gly Ser Glu Asn Asp Ala Leu
                 85                  90                  95

Tyr Glu Tyr Leu Arg Gln Ser Val Gly Asn Glu Ala Glu Ile Trp Leu
                100                 105                 110

Gly Leu Asn Lys Arg Trp Ser Arg Tyr Phe Trp Val Asp Met Thr Gly
                115                 120                 125

Thr Arg Ile Ala Tyr Lys Asn Trp Met Leu Glu Lys Asp Ala Gln Pro
130                 135                 140

Asp Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
                180
```

<210> SEQ ID NO 63
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 63

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
            100                 105                 110

Gly Leu Asn Lys Arg Trp Ser Arg Tyr Phe Trp Val Asp Met Thr Gly
        115                 120                 125

Thr Arg Ile Ala Tyr Lys Asn Trp Gly Arg Lys Glu Asp Ala Gln Pro
    130                 135                 140

Asp Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 64
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 64

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
            100                 105                 110

```
Gly Leu Asn Lys Arg Trp Ser Arg Tyr Phe Trp Val Asp Met Thr Gly
            115                 120                 125

Thr Arg Ile Ala Tyr Lys Asn Trp Ala Arg Thr Gln Asp Ala Gln Pro
    130                 135                 140

Asp Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 65
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 65

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
            100                 105                 110

Gly Leu Asn Lys Arg Trp Ser Arg Tyr Phe Trp Val Asp Met Thr Gly
            115                 120                 125

Thr Arg Ile Ala Tyr Lys Asn Trp Glu Arg Asn Arg Asp Ala Gln Pro
    130                 135                 140

Asp Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 66
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 66

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30
```

```
Leu Ala Gln Glu Val Ala Leu Leu Lys Glu Gln Gln Ala Leu Gln Thr
        35                  40                  45
Val Cys Leu Lys Gly Thr Lys Val His Met Lys Cys Phe Leu Ala Phe
 50                  55                  60
Thr Gln Thr Lys Thr Phe His Glu Ala Ser Glu Asp Cys Ile Ser Arg
 65                  70                  75                  80
Gly Gly Thr Leu Ser Thr Pro Gln Thr Gly Ser Glu Asn Asp Ala Leu
                 85                  90                  95
Tyr Glu Tyr Leu Arg Gln Ser Val Gly Asn Glu Ala Glu Ile Trp Leu
                100                 105                 110
Gly Leu Asn Lys Arg Trp Ser Arg Tyr Phe Trp Val Asp Met Thr Gly
            115                 120                 125
Thr Arg Ile Ala Tyr Lys Asn Trp Val Arg Gln Arg Asp Ala Gln Pro
        130                 135                 140
Asp Pro Ser Asn Trp Glu Asn Cys Ala Val Leu Ser Gly Ala Ala Asn
145                 150                 155                 160
Gly Lys Trp Phe Gly Lys Arg Cys Arg Asp Gln Leu Pro Tyr Ile Cys
                165                 170                 175
Gln Phe Gly Ile Val
            180

<210> SEQ ID NO 67
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 67

Glu Pro Pro Thr Gln Lys Pro Lys Lys Ile Val Asn Ala Lys Lys Asp
1               5                   10                  15
Val Val Asn Thr Lys Met Phe Glu Glu Leu Lys Ser Arg Leu Asp Thr
            20                  25                  30
Leu Ala Gln Glu Val Ala Leu Leu Lys Glu Gln Gln Ala Leu Gln Thr
        35                  40                  45
Val Cys Leu Lys Gly Thr Lys Val His Met Lys Cys Phe Leu Ala Phe
 50                  55                  60
Thr Gln Thr Lys Thr Phe His Glu Ala Ser Glu Asp Cys Ile Ser Arg
 65                  70                  75                  80
Gly Gly Thr Leu Ser Thr Pro Gln Thr Gly Ser Glu Asn Asp Ala Leu
                 85                  90                  95
Tyr Glu Tyr Leu Arg Gln Ser Val Gly Asn Glu Ala Glu Ile Trp Leu
                100                 105                 110
Gly Leu Asn Lys Arg Trp Ser Arg Tyr Phe Trp Val Asp Met Thr Gly
            115                 120                 125
Thr Arg Ile Ala Tyr Lys Asn Trp Glu Arg Pro Glu Asp Ala Gln Pro
        130                 135                 140
Asp Pro Ser Asn Trp Glu Asn Cys Ala Val Leu Ser Gly Ala Ala Asn
145                 150                 155                 160
Gly Lys Trp Phe Gly Lys Arg Cys Arg Asp Gln Leu Pro Tyr Ile Cys
                165                 170                 175
Gln Phe Gly Ile Val
            180

<210> SEQ ID NO 68
```

```
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 68

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
            100                 105                 110

Gly Leu Asn Lys Arg Trp Ser Arg Tyr Phe Trp Val Asp Met Thr Gly
        115                 120                 125

Thr Arg Ile Ala Tyr Lys Asn Trp Ser Arg Gln Glu Asp Ala Gln Pro
    130                 135                 140

Asp Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 69
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 69

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
            100                 105                 110

Gly Leu Asn Lys Arg Trp Ser Arg Tyr Phe Trp Val Asp Met Thr Gly
        115                 120                 125
```

```
Thr Arg Ile Ala Tyr Lys Asn Trp Glu Arg Leu Arg Asp Ser Gln Pro
        130                 135                 140

Asp Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 70
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 70

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
            100                 105                 110

Gly Leu Asn Lys Arg Trp Ser Arg Tyr Phe Trp Val Asp Met Thr Gly
        115                 120                 125

Thr Arg Ile Ala Tyr Lys Asn Trp Ala Ser Met Lys Asp Ala Gln Pro
    130                 135                 140

Asp Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 71
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 71

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45
```

```
Val Cys Leu Lys Gly Thr Lys Val His Met Lys Cys Phe Leu Ala Phe
 50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
                100                 105                 110

Gly Leu Asn Lys Arg Trp Ser Arg Tyr Phe Trp Val Asp Met Thr Gly
                115                 120                 125

Thr Arg Ile Ala Tyr Lys Asn Trp Gln Leu Pro Gln His Ala Asp Pro
                130                 135                 140

Ala Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
                180

<210> SEQ ID NO 72
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 72

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
                20                  25                  30

Leu Ala Gln Glu Val Ala Leu Leu Lys Glu Gln Gln Ala Leu Gln Thr
                35                  40                  45

Val Cys Leu Lys Gly Thr Lys Val His Met Lys Cys Phe Leu Ala Phe
 50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
                100                 105                 110

Gly Leu Asn Lys Arg Trp Ser Arg Tyr Phe Trp Val Asp Met Thr Gly
                115                 120                 125

Thr Arg Ile Ala Tyr Lys Asn Trp Leu Leu Pro Gln His Glu Gln Pro
                130                 135                 140

Glu Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
                180

<210> SEQ ID NO 73
<211> LENGTH: 181
<212> TYPE: PRT
```

<213> ORGANISM: Artificial Sequence
<220> FEATURE:
<223> OTHER INFORMATION: Description of Artificial Sequence: Synthetic
     protein construct

<400> SEQUENCE: 73

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
            100                 105                 110

Gly Leu Asn Lys Arg Trp Ser Arg Tyr Phe Trp Val Asp Met Thr Gly
        115                 120                 125

Thr Arg Ile Ala Tyr Lys Asn Trp Glu Leu Ala Ser Asp Ala Gln Pro
    130                 135                 140

Asp Pro Ala Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 74
<211> LENGTH: 181
<212> TYPE: PRT
<213> ORGANISM: Artificial Sequence
<220> FEATURE:
<223> OTHER INFORMATION: Description of Artificial Sequence: Synthetic
     protein construct

<400> SEQUENCE: 74

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
            100                 105                 110

Gly Leu Asn Lys Arg Trp Ser Arg Tyr Phe Trp Val Asp Met Thr Gly
        115                 120                 125

Thr Arg Ile Ala Tyr Lys Asn Trp Glu Leu Ile Arg Asp Ala Gln Pro

```
            130                 135                 140
Asp Pro Ala Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 75
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 75

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
            100                 105                 110

Gly Leu Asn Lys Arg Trp Ser Arg Tyr Phe Trp Val Asp Met Thr Gly
        115                 120                 125

Thr Arg Ile Ala Tyr Lys Asn Trp Glu Leu Leu Ser Asp Ala Gln Pro
    130                 135                 140

Asp Pro Val Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 76
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 76

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
```

```
                50                  55                  60
Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
                100                 105                 110

Gly Leu Asn Lys Arg Trp Ser Arg Tyr Phe Trp Val Asp Met Thr Gly
            115                 120                 125

Thr Arg Ile Ala Tyr Lys Asn Trp Glu Arg Arg Gln Asp Ala Gln Pro
        130                 135                 140

Asp Pro Ser Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 77
<211> LENGTH: 181
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 77

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
                20                  25                  30

Leu Ala Gln Glu Val Ala Leu Leu Lys Glu Gln Gln Ala Leu Gln Thr
            35                  40                  45

Val Cys Leu Lys Gly Thr Lys Val His Met Lys Cys Phe Leu Ala Phe
        50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
                100                 105                 110

Gly Leu Asn Lys Arg Trp Ser Arg Tyr Phe Trp Val Asp Met Thr Gly
            115                 120                 125

Thr Arg Ile Ala Tyr Lys Asn Trp Glu Arg Leu Ala Asp Ala Gln Pro
        130                 135                 140

Asp Pro Phe Asn Trp Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 78
<211> LENGTH: 181
<212> TYPE: PRT
<213> ORGANISM: Artificial Sequence
<220> FEATURE:
```

<223> OTHER INFORMATION: Description of Artificial Sequence: Synthetic
protein construct

<400> SEQUENCE: 78

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
            100                 105                 110

Gly Leu Asn Lys Arg Trp Ser Arg Tyr Phe Trp Val Asp Met Thr Gly
        115                 120                 125

Thr Arg Ile Ala Tyr Lys Asn Trp Glu Gly Ile Glu Trp Ala Gln Pro
    130                 135                 140

Asp Pro Thr Asn Phe Glu Asn Cys Ala Val Leu Ser Gly Ala Ala Asn
145                 150                 155                 160

Gly Lys Trp Phe Gly Lys Arg Cys Arg Asp Gln Leu Pro Tyr Ile Cys
                165                 170                 175

Gln Phe Gly Ile Val
            180

<210> SEQ ID NO 79
<211> LENGTH: 181
<212> TYPE: PRT
<213> ORGANISM: Homo sapiens

<400> SEQUENCE: 79

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
            100                 105                 110

Gly Leu Asn Asp Met Ala Ala Glu Gly Thr Trp Val Asp Met Thr Gly
        115                 120                 125

Thr Arg Ile Ala Tyr Lys Asn Trp Glu Thr Glu Ile Thr Ala Gln Pro
    130                 135                 140

Asp Gly Gly Lys Thr Glu Asn Cys Ala Val Leu Ser Gly Ala Ala Asn
145                 150                 155                 160

```
Gly Lys Trp Phe Asp Lys Arg Cys Arg Asp Gln Leu Pro Tyr Ile Cys
                165                 170                 175

Gln Phe Gly Ile Val
            180

<210> SEQ ID NO 80
<211> LENGTH: 51
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu
    50

<210> SEQ ID NO 81
<211> LENGTH: 73
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 81

Met Gly Ser His His His His His His Gly Ser Ile Gln Gly Arg Ser
1               5                   10                  15

Pro Gly Thr Glu Pro Pro Thr Gln Lys Pro Lys Lys Ile Val Asn Ala
            20                  25                  30

Lys Lys Asp Val Val Asn Thr Lys Met Phe Glu Glu Leu Lys Ser Arg
        35                  40                  45

Leu Asp Thr Leu Ala Gln Glu Val Ala Leu Leu Lys Glu Gln Gln Ala
    50                  55                  60

Leu Gln Thr Val Ser Leu Lys Gly Ser
65                  70

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Glu Arg Thr Thr Asp Ala Gln Pro Asp Pro Ser Asn Trp
1               5                   10
```

US 7,820,622 B2

TNF ANTAGONISTS

CROSS-REFERENCE TO RELATED APPLICATIONS

The application is the National Stage of International Application No. PCT/DK2005/000742 filed on Nov. 21, 2005, which claims priority from DK Application No. 2004 01813, filed on Nov. 22, 2004, and which claims the benefit of U.S. Provisional Application No. 60/629,343, filed on Nov. 22, 2004. Each of these applications is hereby incorporated by reference in their entirety into the present Application.

FIELD OF THE INVENTION

The present invention relates generally to polypeptides and related compounds that can bind and act as antagonists of TNF.

BACKGROUND OF THE INVENTION AND PRIOR ART

Tumour necrosis factor (TNF) is a homotrimeric cytokine produced by numerous cell types, including monocytes and macrophages, that was originally identified based on its capability to induce the necrosis of certain mouse tumor. TNF is one of the principal mediators of the immune and inflammatory response, and it is e.g. known to have an important role in the pathogenesis of rheumatoid arthritis, which is a common autoimmune inflammatory disease that affects approximately 0.5-1% of the human population. Additionally, TNF is also known to be involved in the pathogenesis of a wide range of disease states, including endotoxin shock, cerebral malaria and graft-versus-host reaction. The soluble and bioactive form of TNF consists of three identical 17 kD protein subunits (homotrimeric), whereas the membrane bound form consist of three identical 26 kD subunits.

Recombinant or modified proteins are an emerging class of therapeutic agents. To date, several recombinant or modified proteins which acts as TNF antagonists have been disclosed. In particular, antibodies that bind to and neutralise TNF have been sought as a means to inhibit TNF activity. Infliximab (Remicade) and Eternarcept (Enbrel) are examples of two TNF antagonists which have both received marketing authorization in the United States and Europe for treatment of rheumatoid arthritis. The two products have also been shown to be effective for the treatment of psoriasis and Chrohn's disease. Infliximab is a chimeric antibody with murine variable regions and human IgG1 and κ constant regions, which neutralises the biological activity of TNF by binding to the soluble and transmembrane forms of TNF and inhibits the binding of TNF with its receptors. The structure of Infliximab is similar to that of naturally occurring antibodies. Eternacept is a fusion protein made up of the extracellular domain of the p75 TNF receptor and the hinge and Fc domains of human IgG1.

WO 2004/0398 discloses four specific binding polypeptides based on human tetranectin C-type lectin like domains (CTLD) which are capable of binding TNF. The proteins are differing from the wild-type CTLD by the amino acid sequence KVRSRYF in the loop 1 region (tetranectin amino acids nos. 116-122 in SEQ ID NO:79), and PRHT, PTNN, PTNR, or PNNR in the loop 3/4 region (tetranectin amino acids nos. 146-149 in SEQ ID NO:79) (cf. WO 2004/0398, Table 4, page 46).

The present inventors have identified and isolated specific TNF binding proteins based on human tetranectin C-type lectin like domains with improved binding characteristics and improved efficacy. The identified TNF binding proteins are superior to the above prior art CTLD based TNF binding proteins i.a. in terms of their in vivo capability of inhibiting and neutralising TNF. This has e.g. been demonstrated by their capability to inhibit TNF alpha mediated cytotoxicity in a murine fibroblast cell line assay, as will be apparent from the following examples. Additionally, the isolated specific TNF binding proteins have also been demonstrated to have superior TNF antagonistic characteristics as compared to the commercially available TNF antagonists Infliximab (Remicade) and Eternarcept (Enbrel).

SUMMARY OF THE INVENTION

Accordingly, the invention relates in a first aspect to a polypeptide capable of binding tumour necrosis factor (TNF), where the polypeptide comprises a TNF binding domain comprising the amino acid sequence KRWSRYF (SEQ ID NO:1).

In further aspects the invention provides a nucleic acid which comprises a sequence encoding a polypeptide as defined above, and methods of preparing specific polypeptides of the invention which comprise expressing said nucleic acids under such conditions that the specific polypeptides are expressed, and recovering the specific polypeptides.

The polypeptides according to the invention may be used for the preparation of pharmaceutical compositions, and in a method of treatment of a subject having a pathology mediated by TNF, such as a method of treatment of rheumatoid arthritis, which comprises administering to the subject an effective amount of the specific binding agent of the invention.

These and other aspects of the invention are described in further detail below.

DETAILED DESCRIPTION OF THE INVENTION

The present invention pertains to polypeptides which bind to TNF with high affinity, low off-rate and have a high tumor necrosis factor (TNF) neutralising capacity.

As mentioned above, the polypeptides of the present invention are derived from the scaffold structure of Tetranectin C-type lectin-like domains (CTLD). The C-type lectin-like domain (CTLD) is a protein domain family which has been identified in a number of proteins isolated from many animal species. Initially, the CTLD domain was identified as a domain common to the so-called C-type lectins (calcium-dependent carbohydrate binding proteins) and named "Carbohydrate Recognition Domain" ("CRD"). More recently, it has become evident that this domain is shared among many eukaryotic proteins such as tetranectin, of which several do not bind sugar moieties, and hence, the canonical domain has been named as CTLD. The CTLD consists of approximately 120 amino acid residues and, characteristically, contains two or three intra-chain disulfide bridges.

The CTLD domain has previously been disclosed in WO/0248189 as suitable for the generation of randomised libraries of ligand-binding protein units. The libraries were constructed by combining a tetranectin CTLD framework structure in which the CTLD's loop-region was partially or completely replaced with one or more randomised polypeptide segments.

The polypeptides of the present invention were constructed by the use of such a randomised library system, in which the CTLD domain of tetranectin was used for the construction of novel TNF binding polypeptides. The TNF binding polypeptides according to the invention have reached their high binding affinity and in vivo capability of inhibiting and neutralising TNF, through a sequence of carefully managed in vitro evolution steps. In general the method implies taking a first candidate polypeptide of high specificity, but poor affinity, through consecutive steps of affinity and binding kinetics maturation. The polypeptides according to the invention are "offspring" from several selection and maturation steps.

It will be appreciated that the invention relates to a polypeptide which is capable of binding and preferably neutralising TNF, where the polypeptide comprises an amino acid sequence as set out as SEQ ID NO:1. The amino acid sequence has been generated in the so-called loop 1 region in the tetranectin CTLD framework (amino acids nos. 116-122 in SEQ ID NO:79). This sequence provides particularly advantageous characteristics, including high TNF neutralising activity. The amino acid sequence is set forth in Table 1 below:

TABLE 1

| SEQ ID NO. | Amino acid sequence |
|---|---|
| 1 | KRWSRYF |

The TNF binding polypeptides of the present invention are capable of binding portions of TNF. In accordance with the invention, the term "capable of binding tumour necrosis factor (TNF)" refers to a specific polypeptide which binds to TNF. In useful embodiments, the TNF binding polypeptides of the invention have a binding affinity (Kd) for the TNF that preferably is $1\times10^{-8}$ M or less determined by surface plasmon resonance. In other useful embodiments, the Kd value is less than $1\times10^{-9}$ M, $1\times10^{-10}$ M, $1\times10^{-11}$ M, $1\times10^{-12}$ M, $1\times10^{-13}$ M, $1\times10^{-14}$ M, or even less than $1\times10^{-15}$ M. In further useful embodiments, the K-off rate for the TNF binding polypeptides according to the invention is less than $1\times10^{-3}$ $S^{-1}$, such as less than $1\times10^{-4}$ $S^{-1}$, including less than $1\times10^{-5}$ $S^{-1}$, and even less than $1\times10^{-6}$ $S^{-1}$ determined by surface plasmon resonance. The term "K-off", as used herein, is intended to refer to the off rate constant for dissociation of a TNF binding polypeptide according to the invention from the TNF binding polypeptide/TNF complex. The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden).

Preferably, the TNF binding polypeptides of the present invention are capable of binding to TNF in such a manner that they partially or fully block, inhibit, or neutralise the biological activity of TNF and/or other TNF-associated activities. As used herein, the expression "neutralise" means the inhibition of or reduction in biological activity of TNF as measured in vivo or in vitro. The TNF neutralising or antagonistic activity of the polypeptide according to the invention can be demonstrated by an in vitro assay such as the murine fibroblast L929 cell line assay or the HUVEC assay described in the Examples below. Alternatively, it may be appropriate to measure the TNF antagonistic activity by in vivo animal testing by e.g. applying the Tg197 transgenic mice line described as described in the Examples below.

In the present context, the term "tumor necrosis factor" (abbreviated herein as TNF) as used herein is intended to refer to a human cytokine that in its soluble and biologically active form consists of three identical 17 kD non-covalently bound protein subunits, whereas the membrane bound form consist of three identical 26 kD protein subunits. In particular the term is intended to refer to the protein described under the entry name "TNFA_HUMAN" and primary accession number P01375 in *ExPASy: the proteomics server for in-depth protein knowledge and analysis* Nucleic Acids Res. 31:3784-3788 (2003) (accessible via the internet address www.expasy.org). The structure of TNF is described further in, for example, Pennica D., et al. (1984) Nature 312:724-729. Frequently used synonyms for TNF includes TNF-alpha, Tumor necrosis factor ligand superfamily member 2, TNF-a and Cachectin.

As mentioned above, the polypeptides of the present invention comprises an amino acid sequence substantially as set out as KRWSRYF (SEQ ID NO:1). By "substantially as set out" is meant that the polypeptide of the invention will comprise an amino acid sequence which is either identical or highly homologous to the amino acid sequence KRWSRYF (SEQ ID NO: 1) of the invention. By "highly homologous" it is contemplated that 1, 2, 3 or even 4 out of the seven amino acids in the sequence KRWSRYF (SEQ ID NO: 1) may be substituted by another amino acid. Hence, in accordance with the invention the polypeptide of the invention may comprises an amino acid sequence having at least about 43%, 57%, 71%, 86% amino acid sequence identity with the amino acid sequence KRWSRYF (SEQ ID NO:1). Preferably, the substitutions of the amino acids are conservative substitutions which results in polypeptides having functional and chemical characteristics similar to those of the polypeptide having the original amino acid sequence. Naturally occurring amino acid residues may be divided into (overlapping) classes based on common side chain properties:

(1) Hydrophobic: Alanine (Ala; A), Valine (Val; V), Leucine (Leu; L), Isoleucine (Ile; I), Proline (Pro; P), Tryptophan (Trp; W), Phenylalanine (Phe; F), Tyrosine (Tyr; Y) and Methionine (Met, M);
(2) Hydrophilic: Serine (Ser; S), Threonine (Thr; T), Asparagine (Asn; N), Glutamine (Glu; Q), Glutamic Acid (Glu; E), Aspartic Acid (Asp; D), Lysine (Lys; K), Arginine (Arg; R), Histidine (His; H);
(3) Aromatic: Tryptophan (Trp; W), Tyrosine (Tyr; Y), Phenylalanine (Phe; F);
(4) Acidic: Aspartic Acid (Asp; D), Glutamic Acid (Glu; E);
(5) Basic: Lysine (Lys; K), Arginine (Arg; R), Histidine (His; H);
(6) Charged: Aspartic Acid (Asp; D), Glutamic Acid (Glu; E), Lysine (Lys; K), Arginine (Arg; R), Histidine (His; H); and
(7) Residues that influence chain orientation: Glycine (Gly; G), Proline (Pro; P).

Conservative amino acid substitutions involve exchanging a member of one of the above amino acid classes for another member of the same class. Conservative changes may encompass unconventional amino acid residues, which are typically incorporated by chemical peptide synthesis rather than by synthesis in biological systems.

As will be apparent from the following Examples, it was found by the inventors that polypeptides of the invention which, in addition to the above sequence KRWSRYF, further comprises the common amino acid sequence motif $PX_1PX_2N$ (SEQ ID NO:2), wherein $X_1$ and $X_2$ are each independently amino acid residues, had particularly advantageous characteristics, including high TNF neutralising activity.

In a further embodiment the polypeptide according to the invention comprises the additional common amino acid sequence motif $X_1PX_2PX_3NX_4$ (SEQ ID NO:3), wherein $X_1$ is a hydrophilic amino acid selected from S, T, N, Q, E, D, K, R and H; $X_2$ and $X_3$ are each independently amino acid residues, and $X_4$ is a hydrophobic amino acid selected from the group consisting of M, A, V, L, P, W, F, Y and C. In a further useful embodiment, the polypeptide according to invention further comprises the amino acid sequence $X_1PX_2PX_3NX_4$ (SEQ ID NO:3), wherein $X_1$ is a hydrophilic amino acid selected from S, T, N, Q, E, D, K, R and H; $X_2$ and $X_3$ are each independently amino acid residues, and $X_4$ is an aromatic amino acid selected from the group consisting of W, F and Y.

In presently preferred embodiments the polypeptide according to the invention comprises an amino acid sequence selected from the group consisting of SEQ ID NOs 2-28 as set forth in Table 2 below:

TABLE 2

| SEQ ID NO | Amino acid sequence |
|---|---|
| 2 | PXPXN |
| 3 | XPXPXNX |
| 4 | ELPQHAQPDPSNW |
| 5 | EHSSDAQPDPSNW |
| 6 | RETTDAQPDPSNW |
| 7 | GRKEDAQPDPSNW |
| 8 | KLPQHANPSPSNW |
| 9 | LLPQHANPNPSNW |
| 10 | KLPQHAHPEPSNW |
| 11 | ALPQHASPSPSNW |
| 12 | MLEKDAQPDPSNW |
| 13 | GRKEDAQPDPSNW |
| 14 | ARTQDAQPDPSNW |
| 15 | ERNRDAQPDPSNW |
| 16 | VRQRDAQPDPSNW |
| 17 | ERPEDAQPDPSNW |
| 18 | SRQEDAQPDPSNW |
| 19 | ERLRDSQPDPSNW |
| 20 | ASMKDAQPDPSNW |
| 21 | QLPQHADPAPSNW |
| 22 | LLPQHEQPEPSNW |
| 23 | ELASDAQPDPANW |
| 24 | ELIRDAQPDPANW |
| 25 | ELLSDAQPDPVNW |
| 26 | ERRQDAQPDPSNW |
| 27 | ERLADAQPDPFNW |
| 28 | EGIEWAQPDPTNF |

It is clearly seen for table 2, that the sequence motif PXPXN (SEQ ID NO: 2) can be found in all of the identified sequences (SEQ ID NOs: 4-28). Therefore, it is contemplated that amino acid substitutions, such as conservative substitutions, may also be applied for the above amino acid sequences shown in Table 2 as previously described above. Thus, it is contemplated that 1, 2, 3, 4, 5, 6, 7, 8, 9 or even 10 out of the 13 amino acids in the sequences SEQ ID NOs: 4-28 may be substituted by another amino acid. Hence, in accordance with the invention the polypeptide of the invention may further comprise an amino acid sequence having at least about 23%, 31%, 38%, 46%, 54%, 62%, 69%, 77%, 85% or 92% amino acid sequence identity with any of the amino acid sequences SEQ ID NOs: 4-28. Preferably, the substitutions of the amino acids are conservative substitutions which results in polypeptides having functional and chemical characteristics similar to those of the polypeptide having the original amino acid sequence.

One skilled in the art will recognise that the various identified amino acid sequences according to the invention may be inserted into specific binding agent structures. Thus, a given amino acid sequence according to the invention may form part or be carried by any suitable proteinaceous framework, provided that the resulting polypeptide retains its capability to bind TNF and preferably neutralise the biological activity of TNF as defined above. However, in preferred embodiments the structure for carrying the generated amino acid sequences of the invention will generally be a C-type lectin-like domain (CTLD) or a substantial portion thereof, in which the generated amino acid sequence SEQ ID NO:1 is located at locations corresponding to the loop 1 region of a CTLD, such as the loop 1 region of human tetranectin amino (acids nos. 116-122 in SEQ ID NO:79). Similarly, the C-type lectin-like domain (CTLD) or a substantial portion thereof may further comprise a generated amino acid sequence selected from SEQ ID NOs 2-28, preferably located at a location corresponding to the loop 3/4 region of the CTLD, such as the loop 1 region of human tetranectin (amino acids nos. 116-122 in SEQ ID NO:79).

In a presently preferred embodiment, the amino acid sequences of the invention are linked to, and thereby carried by, a CTLD framework derived from tetranectin, such as human tetranectin. Preferably, the CTLD domain derived from human tetranectin is an amino acid sequence as substantially set out as residues 50-181 in SEQ ID NO:79.

As will be apparent from the following Examples, it was additionally found by the present inventors, that polypeptides according to invention wherein the C-type lectin-like domain derived from tetranectin is an amino acid sequence as substantially set out as residues 50-181 in SEQ ID NO:79, and wherein the aspartic acid residue no. 165 is mutated to glycine, had particularly good TNF neutralising characteristics.

In one embodiment the polypeptide according to the invention is a monomeric TNF binding polypeptide based on a CTLD framework derived from tetranectin, including a polypeptide such as TN3-2-B1-C22 (SEQ ID NO:29), TN3-2-B1-C31 (SEQ ID NO:30), TN3-2-B1-C24 (SEQ ID NO:31), TN3-2-B1-C22-7 (SEQ ID NO:32), TN3-2-B1-c22-1 (SEQ ID NO:33), TN3-2-B1-c22-2 (SEQ ID NO:34), TN3-2-B1-c22-3 (SEQ ID NO:35), TN3-2-B1-c22-4 (SEQ ID NO:36), TN3-2-B1-c22-6 (SEQ ID NO:37), TN3-2-B1-c22-7 (SEQ ID NO:38), TN3-2-B1-c22-8 (SEQ ID NO:39), TN3-2-B1-c22-9 (SEQ ID NO:40), TN3-2-B1-c22-10 (SEQ ID NO:41), TN3-2-B1-c22-11 (SEQ ID NO:42), TN3-2-B1-c22-12 (SEQ ID NO:43), TN3-2-B1-c22-13 (SEQ ID NO:44), TN3-2-B1-c22-14 (SEQ ID NO:45), TN3-2-B1-c22-15 (SEQ ID NO:46), TN3-2-B1-c22-16 (SEQ ID NO:47), TN3-2-B1-c7 (SEQ ID NO:48), TN3-2-B1-C19 (SEQ ID NO:49), TN3-2-B1-C1 (SEQ ID NO:50), TN3-2-B1-C20 (SEQ ID NO:51), TN3-2-B1-C53 (SEQ ID NO:52) and TN3-2-B1-C29 (SEQ ID NO:53).

In order to provide improved efficacy or neutralising capacity, reduce toxicity, reduce immunogenicity, extend plasma half-life and/or protection from proteolytic degradation, the polypeptides of to the invention may in useful embodiments be coupled to a vehicle through the N-terminus or the C-terminus or a side chain of one of the amino acid residues. Exemplary vehicles include Fc domains, linear polymers such as polyethylene glycol (PEG), polylysine, dextran; a branched chain polymer; a lipid; a cholesterol group (such as a steroid); a carbohydrate or oligosaccharide; or any natural or synthetic protein, polypeptide or peptide, including human serum albumin. One example of polypeptide according to the invention which is coupled to a vehicle is the pegylated TNF binding polypeptide designated GG-I10-TN-2-B1-C22-7 which can seen in Example 5.

In a particularly preferred embodiment, the TNF binding polypeptides of the invention are carried by or linked to a multimerisation domain. In the present context, the term "multimerisation domain" is a peptide, a protein or part of a protein which is capable of interacting with other, similar or identical multimerisation domains. The interaction is of the type that produces multimeric proteins or polypeptides. Such an interaction may be caused by covalent bonds between the components of the multimerisation domains as well as by hydrogen bond forces, hydrophobic forces, van der Waals forces and salt bridges. In useful embodiments, the multimerisation domain peptide is a dimerising domain, a trimerising domain, a tetramerising domain, a pentamerising domain or a hexamerising domain. One example of a trimerising domain is disclosed in WO 95/31540, which describes polypeptides comprising a collectin neck region. The amino acid sequence constituting the collectin neck region may be attached to any polypeptide of choice. Trimers can then be made under appropriate conditions with three polypeptides comprising the collectin neck region amino acid sequence.

In a presently preferred embodiment, the C-type lectin-like domain is carried by and linked to a trimerising domain derived from tetranectin, and more specifically comprises the tetranectin trimerising structural element (hereafter termed TTSE) which has previously been described in detail in WO 98/56906. The amino acid sequence of TTSE is shown in SEQ ID NO:80. The trimerising effect of TTSE is caused by a coiled coil structure which interacts with the coiled coil structure of two other TTSEs to form a triple alpha helical coiled coil trimer which is exceptionally stable even at relatively high temperatures. The term TTSE is also intended to embrace variants of a TTSE of a naturally occurring member of the tetranectin family of proteins, variants which have been modified in the amino acid sequence without adversely affecting, to any substantial degree, the capability of the TTSE to form alpha helical coiled coil trimers. Thus, the polypeptide according to the invention may comprise a TTSE as a trimerising domain, which comprises a sequence having at least 68% amino acid sequence identity with the sequence of SEQ ID NO:80, such as at least 75%, including at least 87%, such as at least 92%. In accordance herewith, the cystein residue No. 50 of the TTSE (SEQ ID NO:50) may advantageously be mutagenised to serine, threonine, methionine or to any other suitable amino acid residue in order to avoid formation of an unwanted inter-chain disulphide bridge, which could lead to unwanted multimerisation.

In a further embodiment, the TTSE trimerising domain (SEQ ID NO:50) may be modified by (i) the incorporation of polyhistidine sequence and/or a cleavage site for the Blood Coagulating Factor $X_a$, (ii) replacing Cys 50 with Ser, and (iii) by including a C-terminal KGS sequence. An example of such a modified TTSE is given as SEQ ID NO:81, and is designated TripA.

Several examples of different trimeric polypeptides in accordance with the invention are provided in the following in examples, in which the above TTSE trimerising domain has been applied. These includes the trimeric CTLD based TNF binding polypeptides: TN2-2-B1-C22 (SEQ ID NO:54), TN2-2-B1-C31 (SEQ ID NO:55), TN2-2-B1-C24 (SEQ ID NO:56), TN2-2-B1-C22-7 (SEQ ID NO:57), TN2-2-B1-c22-1 (SEQ ID NO:58), TN2-2-B1-c22-2 (SEQ ID NO:59), TN2-2-B1-c22-3 (SEQ ID NO:60), TN2-2-B1-c22-4 (SEQ ID NO:61), TN2-2-B1-c22-6 (SEQ ID NO:62), TN2-2-B1-c22-7 (SEQ ID NO:63), TN2-2-B1-c22-8 (SEQ ID NO:64), TN2-2-B1-c22-9 (SEQ ID NO:65), TN2-2-B1-c22-10 (SEQ ID NO:66), TN2-2-B1-c22-11 (SEQ ID NO:67), TN2-2-B1-c22-12 (SEQ ID NO:68), TN2-2-B1-c22-13 (SEQ ID NO:69), TN2-2-B1-c22-14 (SEQ ID NO:70), TN2-2-B1-c22-15 (SEQ ID NO:71), TN2-2-B1-c22-16 (SEQ ID NO:72), TN2-2-B1-c7 (SEQ ID NO:73), TN2-2-B1-C19 (SEQ ID NO:74), TN2-2-B1-C1 (SEQ ID NO:75), TN2-2-B1-C20 (SEQ ID NO:76), TN2-2-B1-C53 (SEQ ID NO:77), TN2-2-B1-C29 (SEQ ID NO:78) and GG-I10-TN-2-B1-C22-7 (SEQ ID NO:79).

In accordance with the invention, the TNF binding polypeptide according to the invention may either be linked to the N- or the C-terminal amino acid residue of the trimerising domain. However, it is also envisaged that in certain embodiments it may be advantageous to link a TNF binding polypeptide of the invention to both the N-terminal and the C-terminal of the trimerising domain of the monomer, and thereby providing a trimeric polypeptide comprising six specific polypeptides capable of binding and neutralising TNF.

It will be appreciated that a flexible molecular linker optionally may be interposed between, and covalently join, the TNF binding polypeptide of the invention and the trimerising domain. In certain embodiments, the linker is a polypeptide sequence of about 1-20 amino acid residues. The linker may be less than 10 amino acids, most preferably, 5, 4, 3, 2, or 1. It may be in certain cases that 9, 8, 7 or 6 amino acids are suitable. In useful embodiments the linker is essentially non-immunogenic, not prone to proteolytic cleavage and does not comprise amino acid residues which are known to interact with other residues (e.g. cystein residues).

The present invention further provides an isolated nucleic acid encoding a polypeptide of the present invention. Nucleic acids include DNA and RNA. In a preferred aspect, the present invention provides a nucleic acid which codes for a polypeptide of the invention, including a polypeptide comprising an amino acid sequence as set out as amino acid sequences SEQ ID NO 1, SEQ ID NOs 2-28, SEQ ID NOs 29-53, and more preferably for the entire trimeric polypeptides SEQ ID NOs 54-78.

The present invention also provides constructs in the form of plasmids, vectors, transcription or expression cassettes which comprise at least one nucleic acid as described above. Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press.

The present invention also provides a recombinant host cell which comprises on or more constructs as above. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is *E. coli*.

Expression of the polypeptide of the present invention may conveniently be achieved by culturing under appropriate conditions recombinant host cells containing the nucleic acid, e.g. as described in details in the following Example 2. Preferably, the expression is performed in an expression system from which the desired protein may readily be isolated and refolded in vitro. As a general matter, prokaryotic expression systems are preferred, including E. coli based systems, since high yields of protein can be obtained and efficient purification and refolding strategies are available. Thus, it is well within the abilities and discretion of the skilled artisan, without undue experimentation, to choose an appropriate or favourite expression system. Similarly, once the primary amino acid sequence for the polypeptide of the present invention is chosen, one of ordinary skill in the art can easily design appropriate polynucleotides such as recombinant DNA constructs which will encode the desired proteins, taking into consideration such factors as codon biases in the chosen host, the need for secretion signal sequences in the host, the introduction of proteinase cleavage sites within the signal sequence, and the like. These recombinant DNA constructs may be inserted in-frame into any of a number of expression vectors appropriate to the chosen host. The choice of an appropriate or favourite expression vector is, again, a matter well within the ability and discretion of the skilled practitioner. Preferably, the expression vector will include a strong promoter to drive expression of the recombinant constructs. Finally, the polypeptide of the invention may be isolated using suitable standard procedures well known in the art, and optionally subjected to further processing such as e.g. lyophilization. The polypeptides of the invention may also be produced by chemical synthesis by choosing appropriate materials and reaction conditions which are will known in the art.

The polypeptides of the present invention will usually be administered in the form of a pharmaceutical composition, which may comprise at least one component in addition to the polypeptide, and optionally other therapeutic ingredients. Thus, pharmaceutical compositions according to the present invention, and for use in accordance with the present invention, may comprise, in addition to the active ingredient, a pharmaceutically acceptable excipient, carrier, buffer, stabiliser or other materials well known to those skilled in the art. The materials must be acceptable in the sense of being compatible with the other ingredients and not deleterious to the recipient thereof. In general, methods for the preparation of pharmaceutical compositions include the step of bringing into association the active ingredient and the additional component.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The pharmaceutical composition may be administered alone or in combination with other treatments, either simultaneously or sequentially dependent upon the condition to be treated. Other treatments may include the administration of suitable doses of pain relief drugs such as non-steroidal anti-inflammatory drugs (e.g. aspirin, paracetamol, ibuprofen or ketoprofen) or opitates such as morphine, or anti-emetics.

The therapeutic application of the present invention comprises treating a subject having a pathology mediated by TNF, by administering to the subject a therapeutically effective amount of the polypeptide or the pharmaceutical composition of the invention.

As mentioned above, TNF is one of the principal mediators of the immune and inflammatory response, and it is e.g. known to have an important role in the pathogenesis of wide range of diseases mediated by TNF. As used herein, a "TNF-mediated disease" or "TNF mediated pathology" refers to a TNF related pathology or disease. TNF related pathologies or diseases include, but are not limited to, the following:

(A) acute and chronic immune and autoimmune pathologies, such as, but not limited to, rheumatoid arthritis (RA), juvenile chronic arthritis (JCA), thyroiditis, graft versus host disease (GVHD), scleroderma, diabetes mellitus, Graves' disease, allergy, acute or chronic immune disease associated with an allogenic transplantation, such as, but not limited to, renal transplantation, cardiac transplantation, bone marrow transplantation, liver transplantation, pancreatic transplantation, small intestine transplantation, lung transplantation and skin transplantation;

(B) infections, including, but not limited to, sepsis syndrome, cachexia, circulatory collapse and shock resulting from acute or chronic bacterial infection, acute and chronic parasitic and/or infectious diseases, bacterial, viral or fungal, such as a human immunodeficiency virus (HIV), acquired immunodeficiency syndrome (AIDS) including symptoms of cachexia, autoimmune disorders, AIDS dementia complex and infections);

(C) inflammatory diseases, such as chronic inflammatory pathologies, such as, but not limited to, sarcoidosis, chronic inflammatory bowel disease, ulcerative colitis, and Crohn's pathology; vascular inflammatory pathologies, such as, but not limited to, disseminated intravascular coagulation, atherosclerosis, Kawasaki's pathology and vasculitis syndromes, such as, but not limited to, polyarteritis nodosa, Wegener's granulomatosis, Henoch-Schonlein purpura, giant cell arthritis and microscopic vasculitis of the kidneys; chronic active hepatitis; Sjogren's syndrome; spondyloarthropathies, such as ankylosing spondylitis, psoriatic arthritis and spondylitis, enteropathic arthritis and spondylitis, reactive arthritis and arthritis associated with inflammatory bowel disease; and uveitis;

(D) neurodegenerative diseases, including, but not limited to, demyelinating diseases, such as multiple sclerosis and acute transverse myelitis; myasthenia gravis; extrapyramidal and cerebellar disorders, such as lesions of the corticospinal system; disorders of the basal ganglia or cerebellar disorders; hyperkinetic movement disorders, such as Huntington's chorea and senile chorea; drug-induced movement disorders, such as those induced by drugs which block central nervous system (CNS) dopamine receptors; hypokinetic movement disorders, such as Parkinson's disease; progressive supranuclear palsy; cerebellar and spinocerebellar disorders, such as astructural lesions of the cerebellum; spinocerebellar degenerations (spinal ataxia, Friedreich's ataxia, cerebellar cortical degenerations, multiple systems degenerations (Mencel, Dejerine-Thomas, Shi-Drager, and MachadoJoseph)); and systemic disorders (Refsum's disease, abetalipoproteinemia, ataxia, telangiectasia, and mitochondrial multisystem disorder); disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's syndrome in middle age; diffuse Lewy body disease; senile dementia of Lewy body type; Wernicke-Korsakoff syndrome; chronic alcoholism; primary biliary cirrhosis; cryptogenic fibrosing alveolitis and other fibrotic lung diseases; hemolytic anemia; Creutzfeldt-Jakob disease; subacute sclerosing panencephalitis, Hallervorden-Spatz disease; and dementia pugilistica, or any subset thereof;

(E) malignant pathologies involving TNF-secreting tumors or other malignancies involving TNF, such as, but not limited to, leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or Mycosis fungoides));

(F) cachectic syndromes and other pathologies and diseases involving excess TNF, such as, but not limited to, cachexia of cancer, parasitic disease and heart failure; and (G) alcohol-induced hepatitis and other forms of chronic hepatitis.

The polypeptide of the present invention may be directly administered to the subject or patient in need thereof, via any suitable route, usually by injection into the bloodstream or directly into site of the TNF mediated disease.

For e.g. diagnostic purposes, assay methods and diagnostic kits, the polypeptides of the invention may also be labelled with a detectable or functional label. Detectable labels include radiolabels such as $^{125}$I, $^{131}$I and $^{99}$Tc, and fluorescent probes such as fluorescein, rhodamine, Texas Red, aminomethylcoumarin and phycoerythrin, which may be attached to the polypeptides of the invention using conventional chemistry known in the art of protein labelling. Labels also include enzyme labels such as horseradish peroxidase. Labels further include chemical moieties such as biotin which may be detected via binding to a specific cognate detectable moiety, e.g. labelled avidin. Functional labels include substances which are designed to be targeted to the site of a TNF afflicted area. Such functional labels include toxins such as ricin and enzymes such as bacterial carboxypeptidase or nitroreductase, which are capable of converting prodrugs into active drugs at the site of the TNF afflicted area.

Thus, the present invention also provides for an assay method for the detection of TNF in a sample which comprises (i) contacting the sample with a polypeptide according to the invention, and (ii) detecting the binding of the polypeptide to TNF.

The invention will now be described by way of illustration in the following non-limiting examples and figures.

EXAMPLES

Example 1

Figure 1:
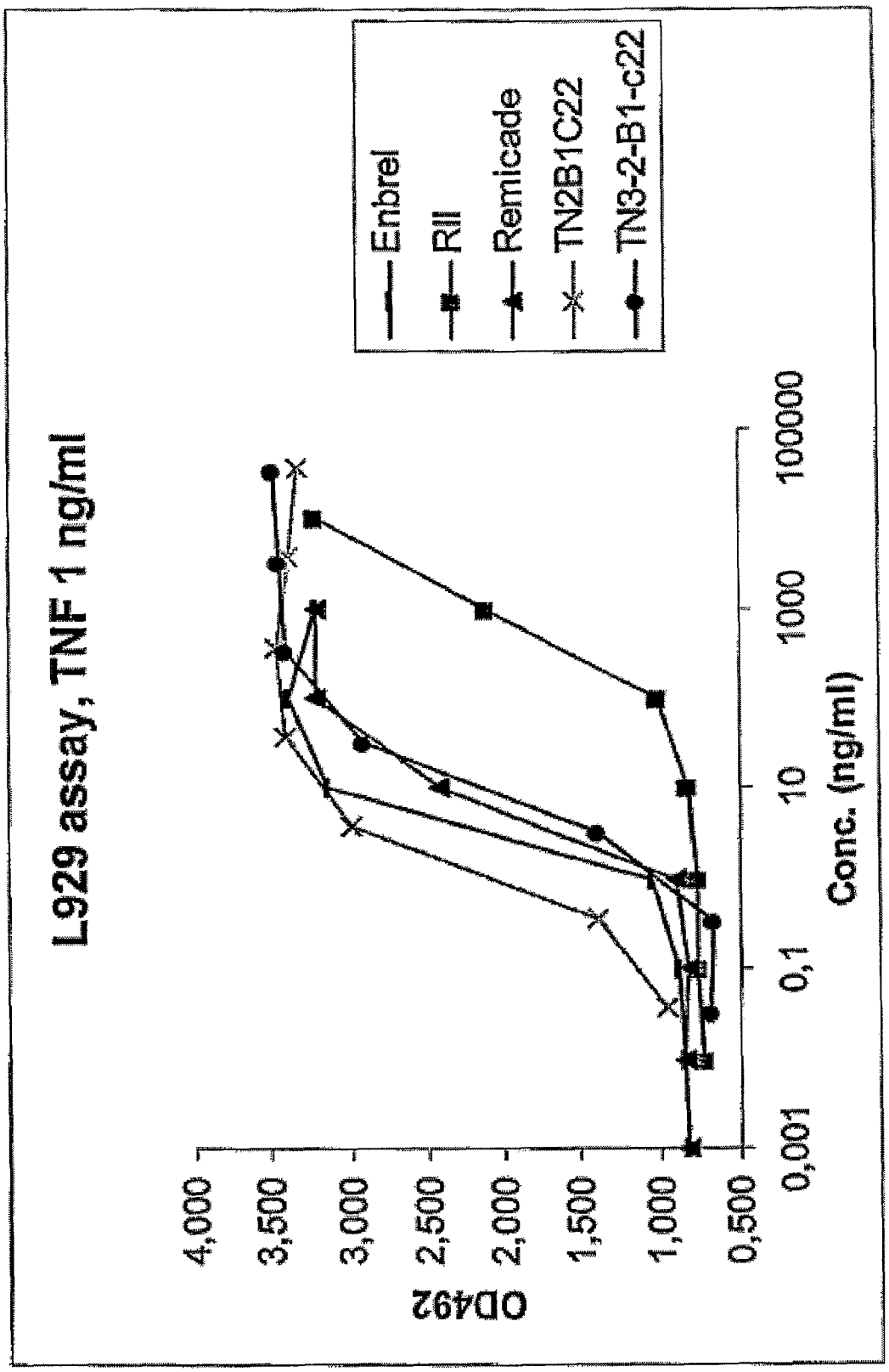
FIG. 1 shows the inhibition of TNF in a L929 cell assay using TNF antagonist TN2-2-B1-C22 as complete trimeric format (TN2B1C22) and as monomer (TN3-2-B1-c22) in comparison to Enbrel, Remicade and TNF receptor II fragment (RII).
Figure 2:
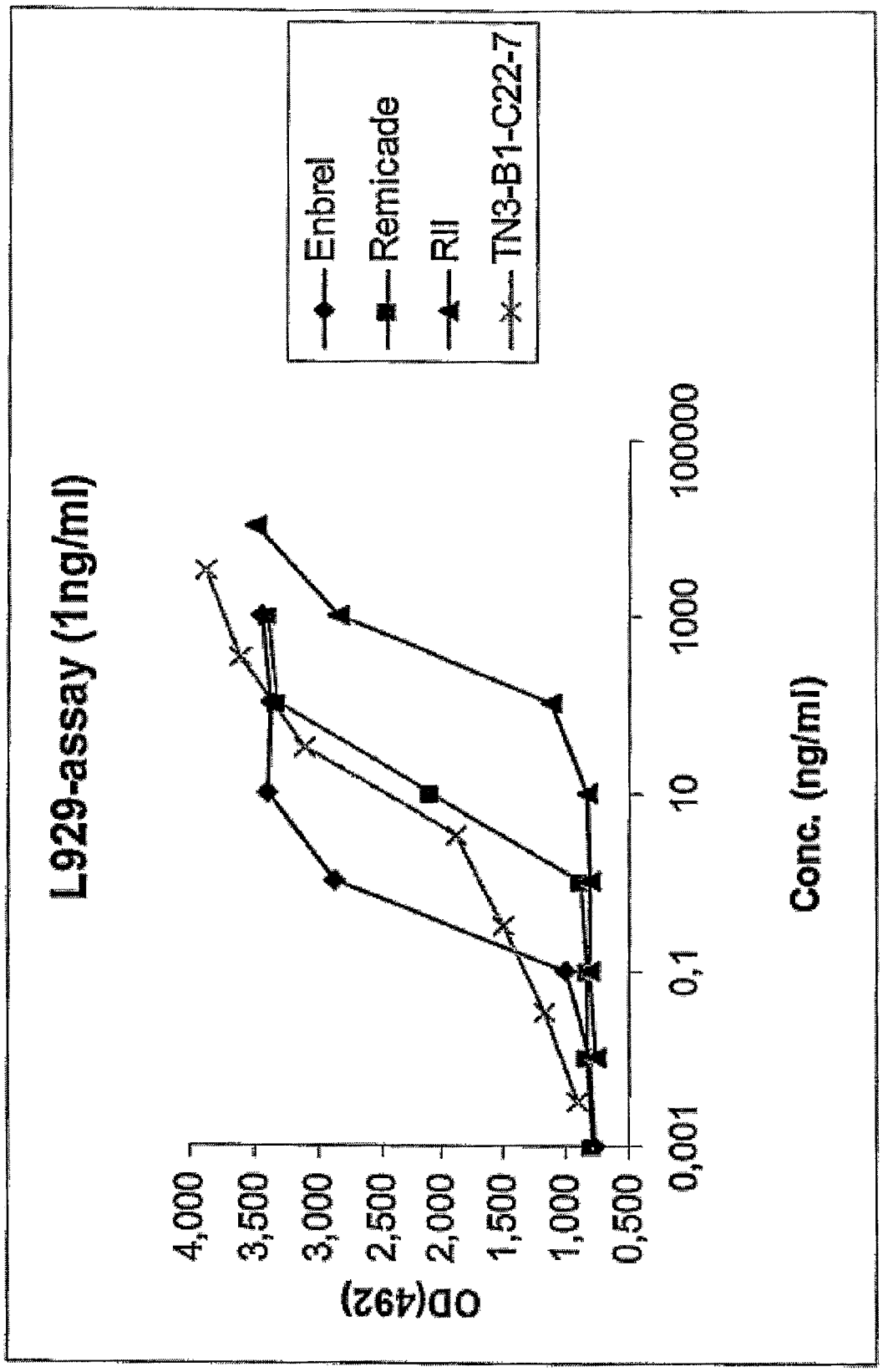
FIG. 2 shows the inhibition of TNF in a L929 cell assay using TNF antagonist TN2-2-B1-C22-7 as monomer (TN3-B1-C22-7) in comparison to Enbrel, Remicade and TNF receptor II fragment (RII).
Figure 3:
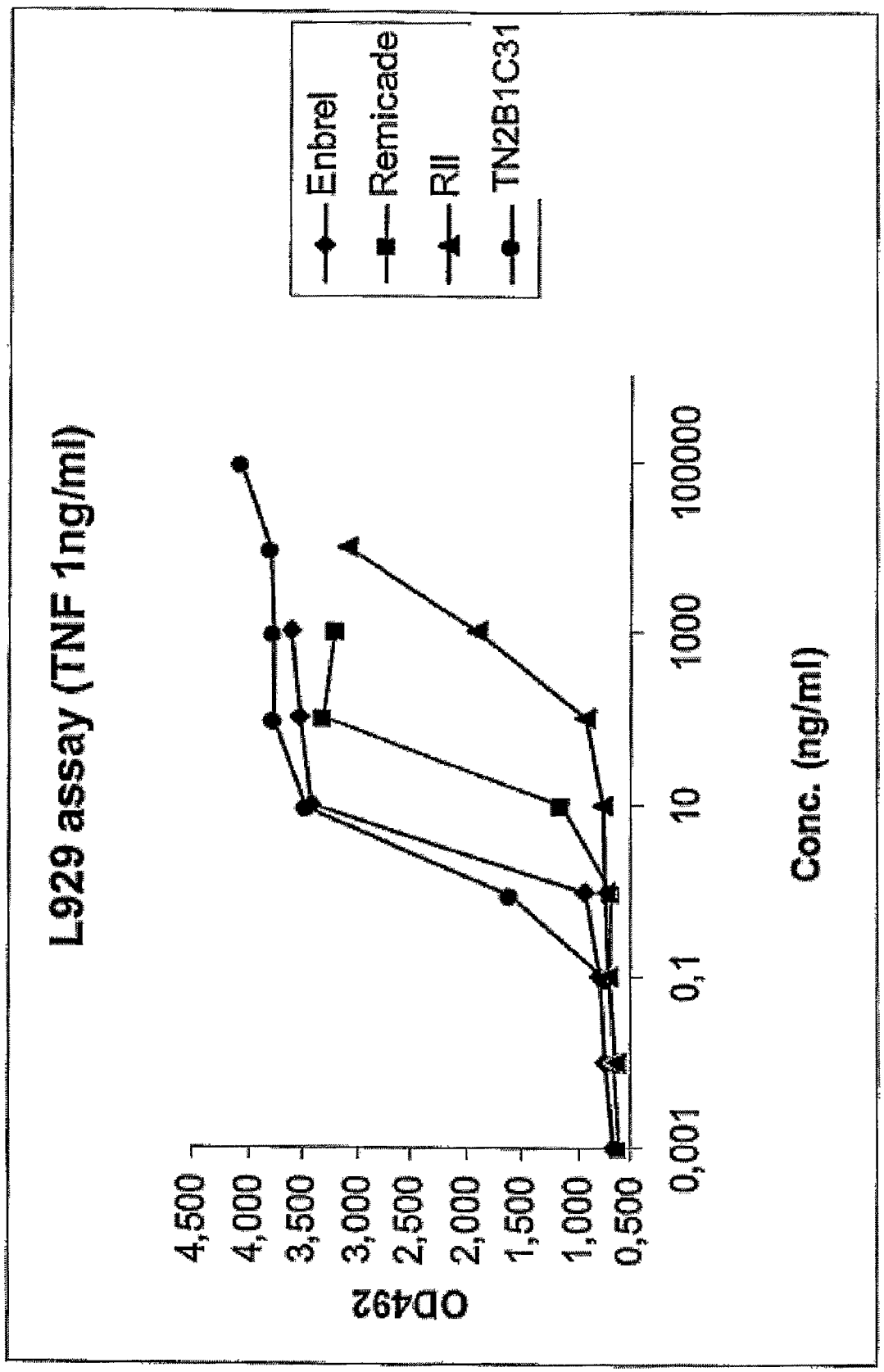
FIG. 3 shows the inhibition of TNF in a L929 cell assay using TNF antagonist TN2-2-B1-C31 as complete trimeric format (TN2B1C31) in comparison to Enbrel, Remicade and TNF receptor II fragment (RII).
Figure 4:
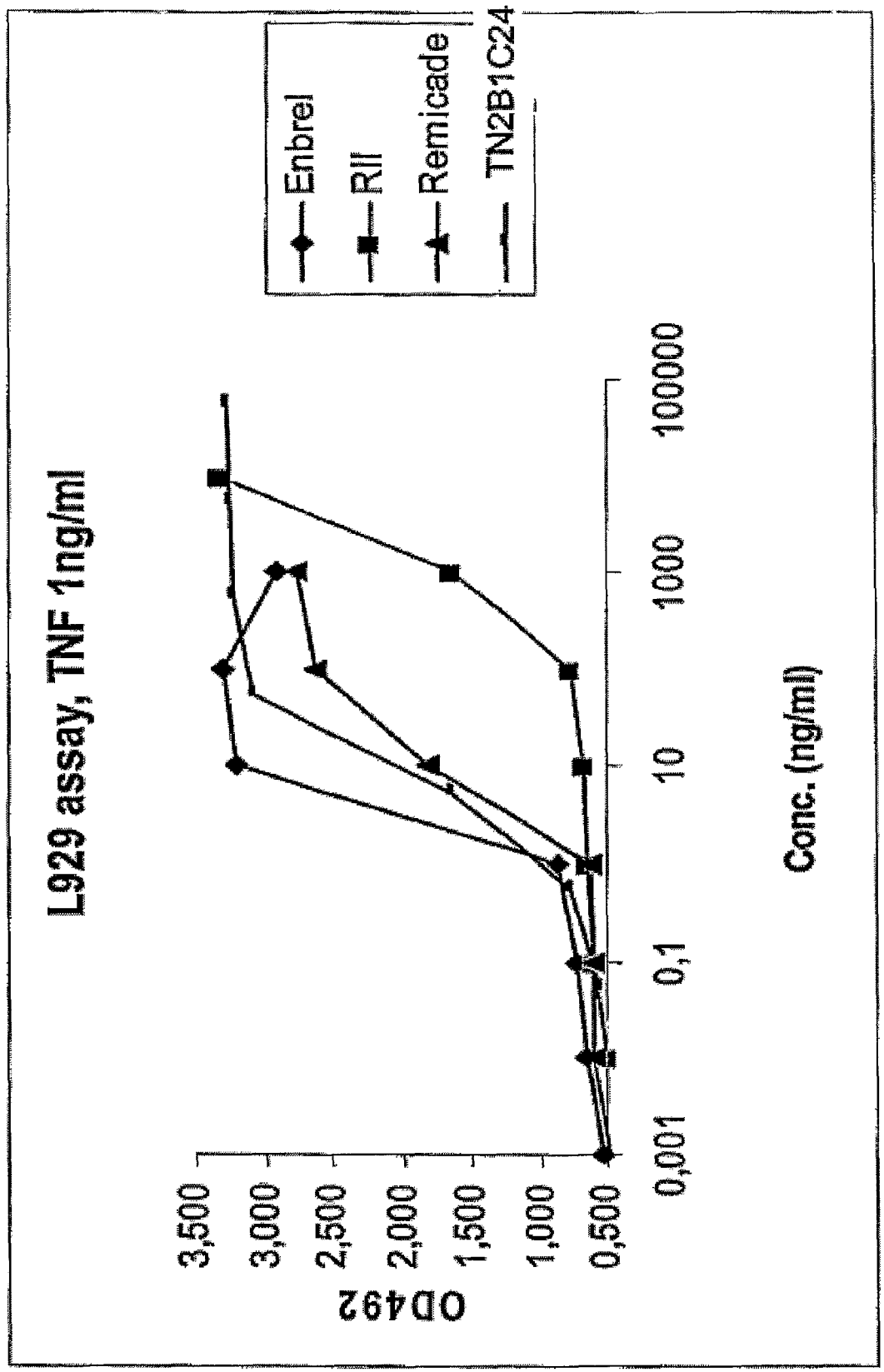
FIG. 4 shows the inhibition of TNF in a L929 cell assay using TNF antagonist TN2-2-B1-C24 as complete trimeric format (TN2B1C24) in comparison to Enbrel, Remicade and TNF receptor II fragment (RII).
Figure 5:
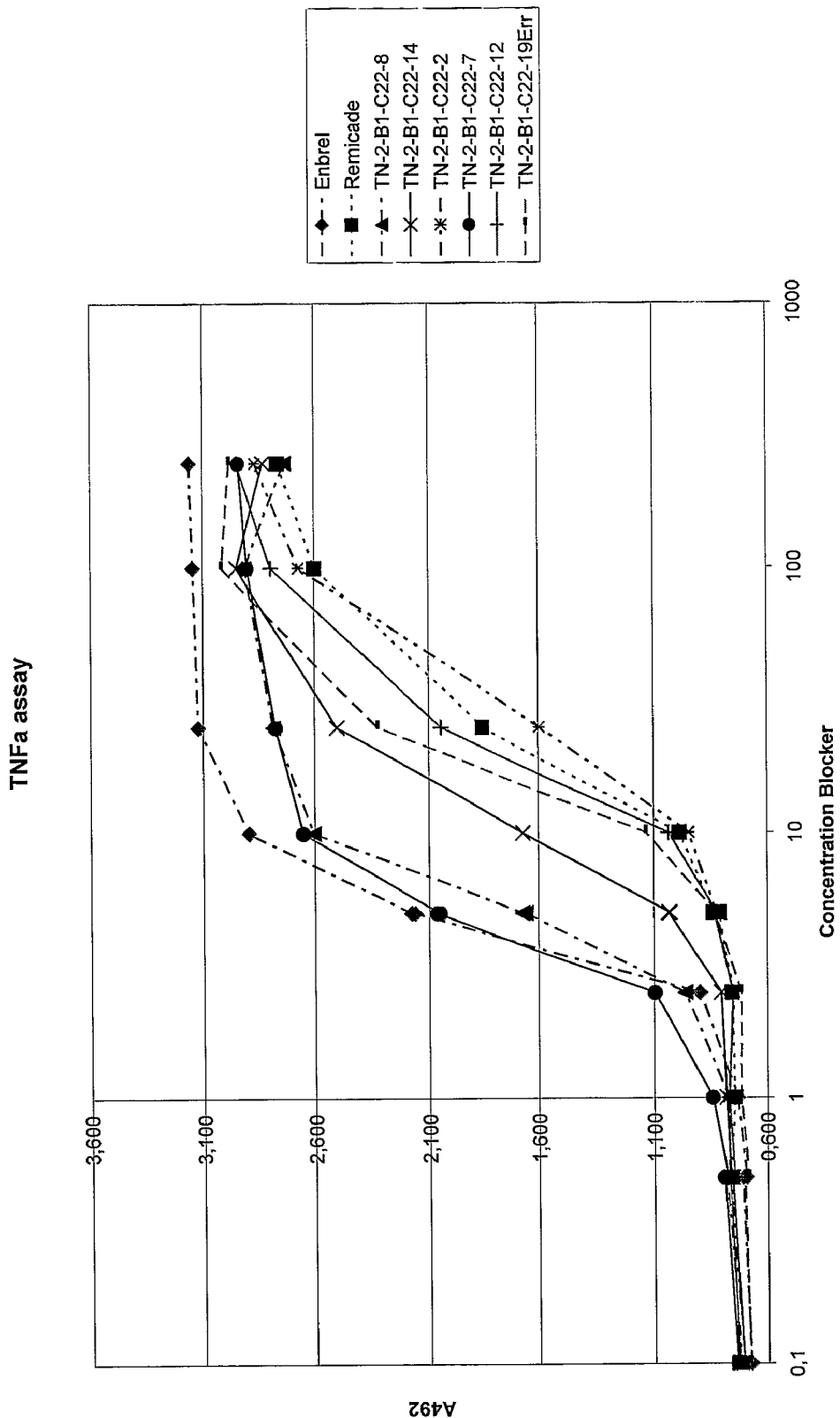
FIG. 5 shows the inhibition of TNF in a L929 cell assay using TNF antagonist TN2-2-B1-C22-8, TN2-2-B1-C22-14, TN2-2-B1-C22-2, TN2-2-B1-C22-7, TN2-2-B1-C22-12, TN2-2-B1-C22-19 in comparison to Enbrel, Remicade and TNF receptor II fragment (RII).
Figure 6:
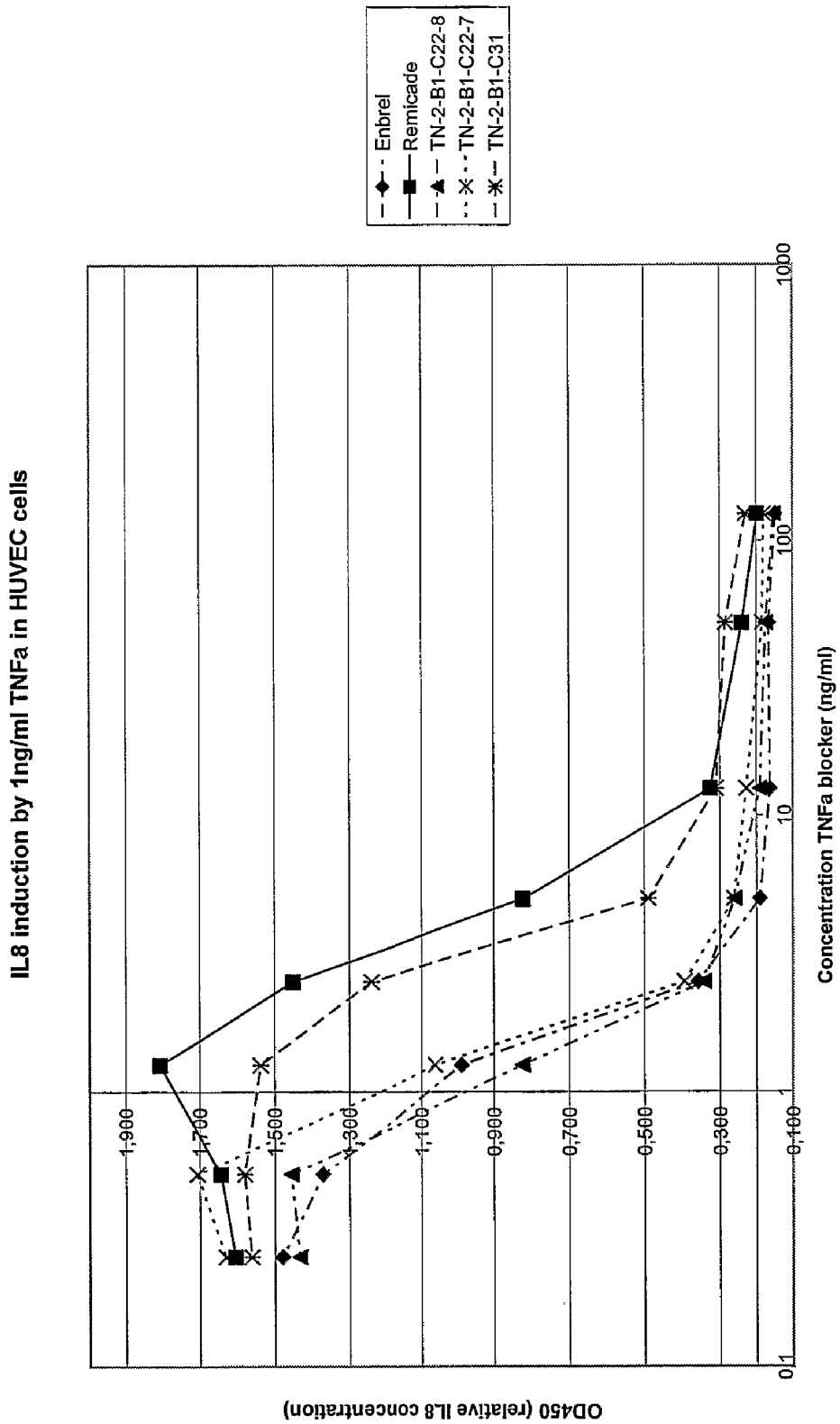
FIG. 6 shows the inhibition of TNF in a L929 cell assay using TNF antagonist TN2-2-B1-C22-8, TN2-2-B1-C22-7 and TN2-2-B1-C31 in comparison to Enbrel and Remicade.
Figure 7:
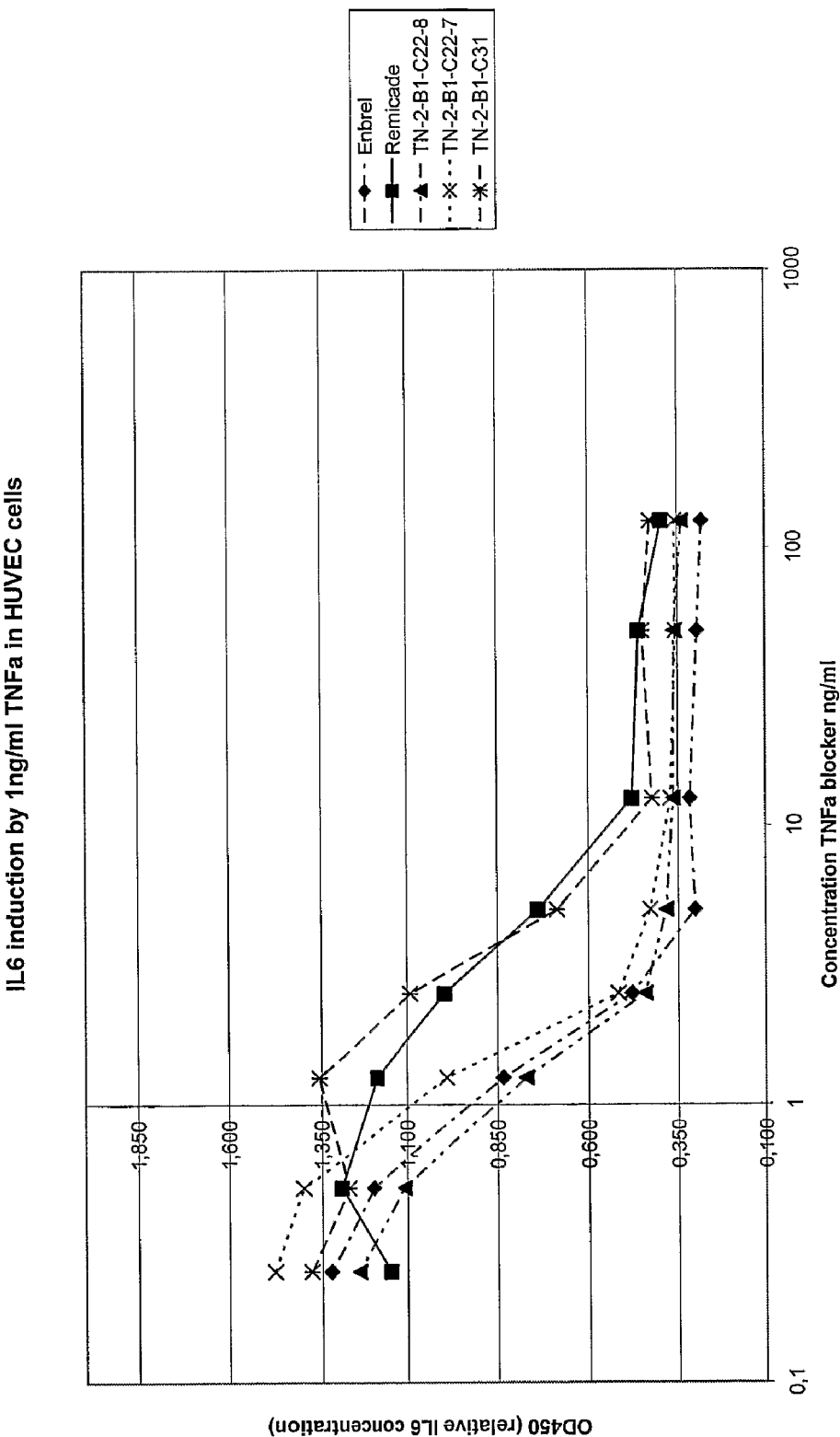
FIG. 7 shows the inhibition of TNF induced IL6 and IL8 production in a HUVEC assay using TN3-2-B1-C31, TN3-2-B1-C22-7, TN3-2-B1-C22-8 in comparison to Enbrel and Remicade.
Figure 8:
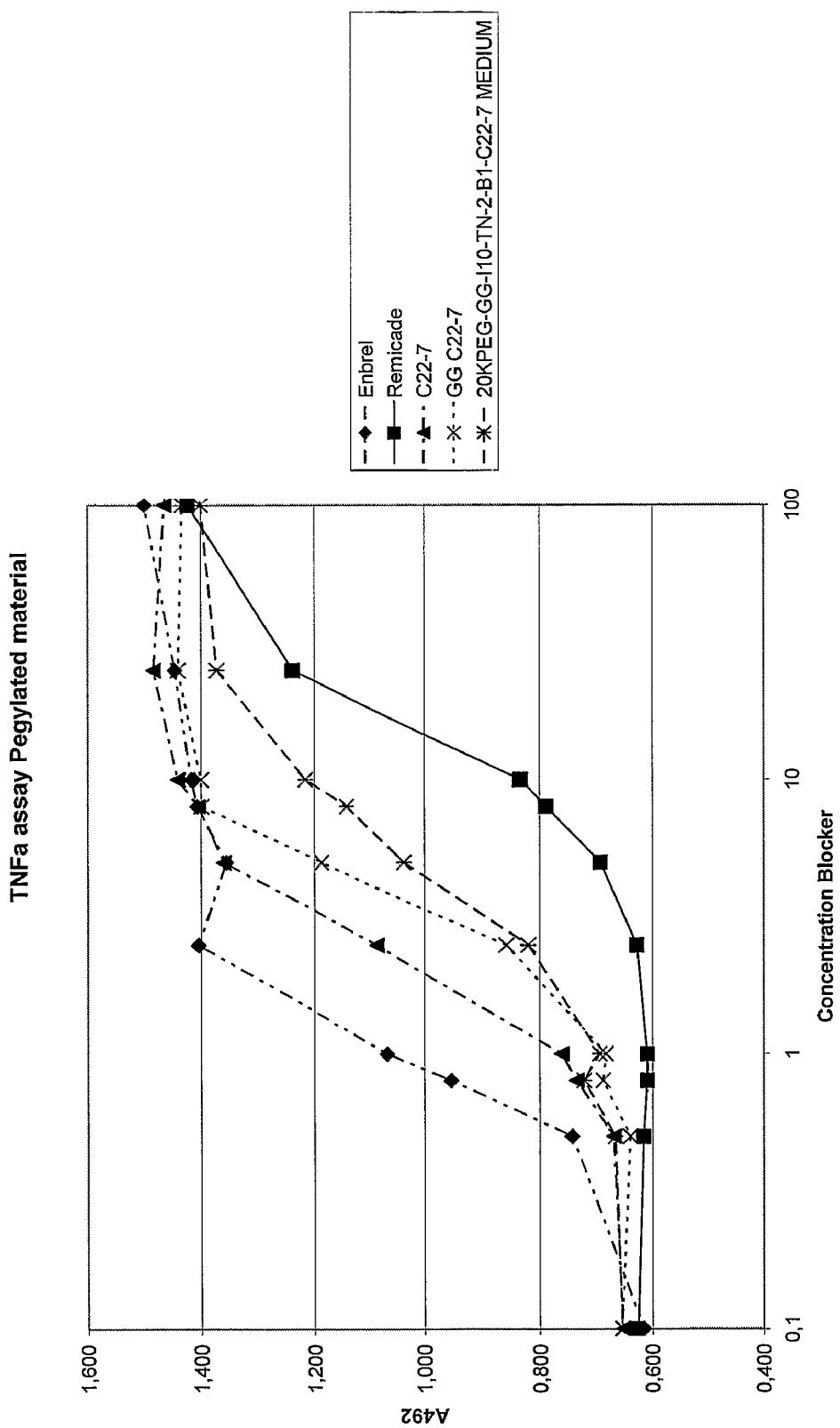
FIG. 8 shows the inhibition of TNF in a L929 cell assay using pegylated GG-I10-TN-2-B1-C22-7 (20KPEG-GG-I10-TN-2-B1-C22-7), non-pegylated GG-I10-TN-2-B1-C22-7 (GG C22-7), and un-mutated TN-2-B1-C22-7 (C22-7) (SEQ ID NO:32). Enbrel and Remicade were used as controls.
Figure 9:
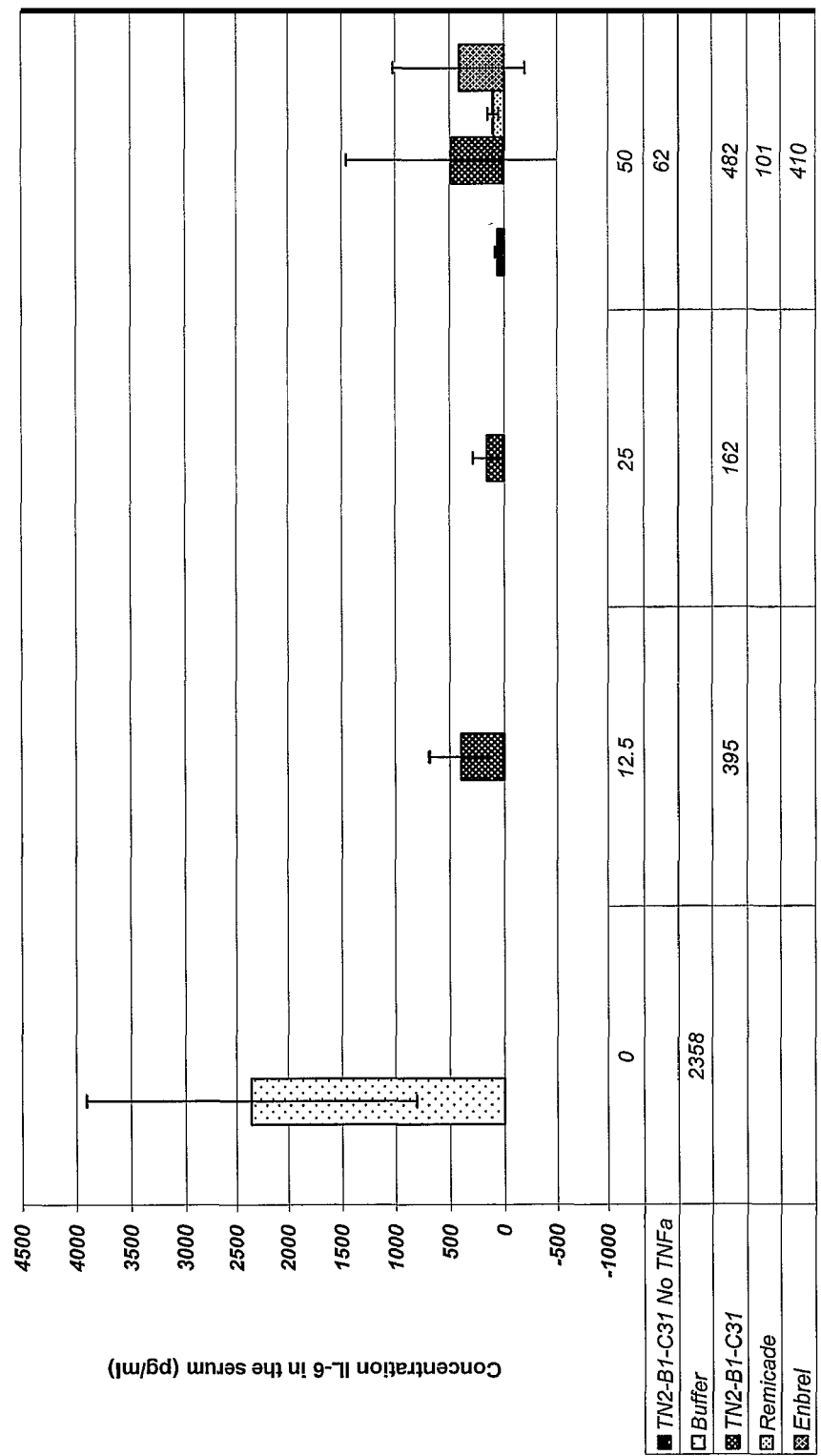
FIG. 9 shows the blocking of TNF induced IL-6 production in mice which were injected with TN2-2-B1-C31 at 3 different concentrations: 12.5, 25 and 50 µg per mouse. After 30 minutes the mice were injected intravenously with 3 µg of human TNF.
Figure 10:
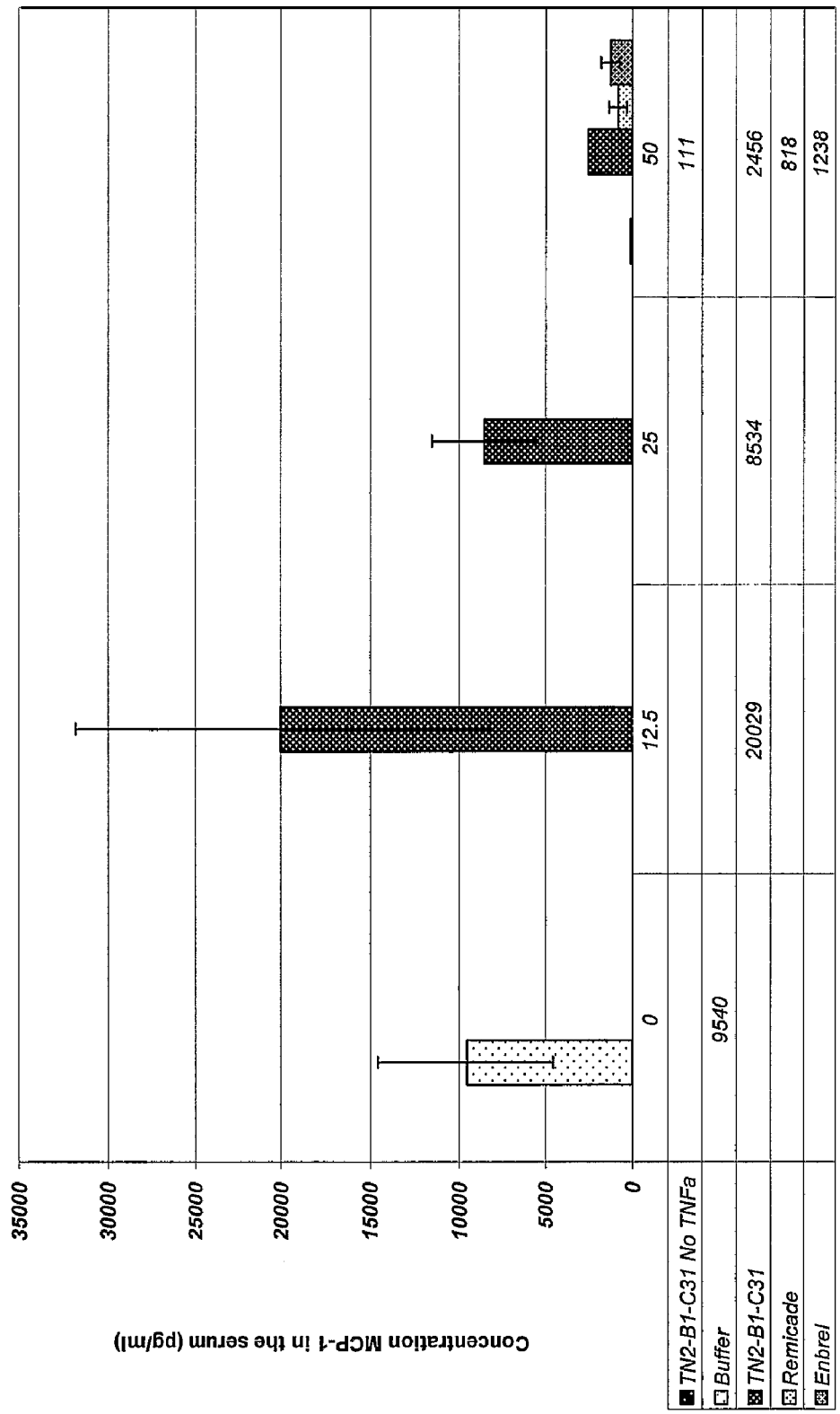
FIG. 10 shows the blocking of TNF induced MCP-1 production in mice which were injected with TN2-2-B1-C31 at 3 different concentrations: 12.5, 25 and 50 µg per mouse. After 30 minutes the mice were injected intravenously with 3 µg of human TNF.

Isolation and Construction of TNF Binding Polypeptides

The scaffold structure of Tetranectin (SEQ ID NO:6) C-type lectin-like domains (CTLD), as previously disclosed in WO/0248189, was used for the isolation and construction of TNF binding polypeptides. The TNF binding polypeptides developed reached their efficacy through a sequence of carefully managed in vitro maturation steps. A first candidate molecule of high specificity, but poor affinity, was taken through consecutive steps of affinity and binding kinetics maturation, the resulting candidates are "offspring" from 3$^{rd}$ and 4$^{th}$ step of maturation. The maturation was performed using phage display technology, essentially as described in WO/0248189.

The identified monomeric CTLD based TNF binding clones are listed below in Table 3, together with their corresponding SEQ ID NOs and loop 1 and loop 3/4 amino acid sequences.

TABLE 3

| Monomeric clone | SEQ ID NO | Loop 1 sequence | Loop 3/4 sequence | Other mutations[a] |
|---|---|---|---|---|
| TN3-2-B1-C22 | 29 | KRWSRYF | ELPQHAQPDPSNW [4] | D165G |
| TN3-2-B1-C31 | 30 | KRWSRYF | EHSSDAQPDPSNW [5] | D165G |
| TN3-2-B1-C24 | 31 | KRWSRYF | ERTTDAQPDPSNW [82] | D165G |
| TN3-2-B1-C22-7 | 32 | KRWSRYF | GRKEDAQPDPSNW [7] | D165G |
| TN3-2-B1-c22-1 | 33 | KRWSRYF | KLPQHANPSPSNW [8] | D165G |
| TN3-2-B1-c22-2 | 34 | KRWSRYF | LLPQHANPNPSNW [9] | D165G |
| TN3-2-B1-c22-3 | 35 | KRWSRYF | KLPQHAHPEPSNW [10] | D165G |
| TN3-2-B1-c22-4 | 36 | KRWSRYF | ALPQHASPSPSNW [11] | D165G |
| TN3-2-B1-c22-6 | 37 | KRWSRYF | MLEKDAQPDPSNW [12] | D165G |
| TN3-2-B1-c22-7 | 38 | KRWSRYF | GRKEDAQPDPSNW [13] | D165G |
| TN3-2-B1-c22-8 | 39 | KRWSRYF | ARTQDAQPDPSNW [14] | D165G |
| TN3-2-B1-c22-9 | 40 | KRWSRYF | ERNRDAQPDPSNW [15] | D165G |
| TN3-2-B1-c22-10 | 41 | KRWSRYF | VRQRDAQPDPSNW [16] | D165G |
| TN3-2-B1-c22-11 | 42 | KRWSRYF | ERPEDAQPDPSNW [17] | D165G |
| TN3-2-B1-c22-12 | 43 | KRWSRYF | SRQEDAQPDPSNW [18] | D165G |
| TN3-2-B1-c22-13 | 44 | KRWSRYF | ERLRDSQPDPSNW [19] | D165G |
| TN3-2-B1-c22-14 | 45 | KRWSRYF | ASMKDAQPDPSNW [20] | D165G |
| TN3-2-B1-c22-15 | 46 | KRWSRYF | QLPQHADPAPSNW [21] | D165G |
| TN3-2-B1-c22-16 | 47 | KRWSRYF | LLPQHEQPEPSNW [22] | D165G |
| TN3-2-B1-c7 | 48 | KRWSRYF | ELASDAQPDPANW [23] | D165G |
| TN3-2-B1-C19 | 49 | KRWSRYF | ELIRDAQPDPANW [24] | D165G |
| TN3-2-B1-C1 | 50 | KRWSRYF | ELLSDAQPDPVNW [25] | D165G |
| TN3-2-B1-C20 | 51 | KRWSRYF | ERRQDAQPDPSNW [26] | D165G |
| TN3-2-B1-C53 | 52 | KRWSRYF | ERLADAQPDPFNW [27] | D165G |
| TN3-2-B1-C29 | 53 | KRWSRYF | EGIEWAQPDPTNF [28] | D165G |

[a]Mutations outside the loop 1 and loop 3/4 location in tetranectin; wt: wild type The identified clones were also produced in trimeric format using the tetranectin trimerising structural element (TTSE; SEQ ID NO:80). The corresponding trimeric versions of the above identified clones are listed in the below Table 4.

TABLE 4

| Trimeric clone | SEQ ID NO | Corresponding monomeric clone |
|---|---|---|
| TN2-2-B1-C22 | 54 | TN3-2-B1-C22 |
| TN2-2-B1-C31 | 55 | TN3-2-B1-C31 |
| TN2-2-B1-C24 | 56 | TN3-2-B1-C24 |
| TN2-2-B1-C22-7 | 57 | TN3-2-B1-C22-7 |
| TN2-2-B1-c22-1 | 58 | TN3-2-B1-c22-1 |
| TN2-2-B1-c22-2 | 59 | TN3-2-B1-c22-2 |
| TN2-2-B1-c22-3 | 60 | TN3-2-B1-c22-3 |
| TN2-2-B1-c22-4 | 61 | TN3-2-B1-c22-4 |
| TN2-2-B1-c22-6 | 62 | TN3-2-B1-c22-6 |
| TN2-2-B1-c22-7 | 63 | TN3-2-B1-c22-7 |
| TN2-2-B1-c22-8 | 64 | TN3-2-B1-c22-8 |
| TN2-2-B1-c22-9 | 65 | TN3-2-B1-c22-9 |
| TN2-2-B1-c22-10 | 66 | TN3-2-B1-c22-10 |
| TN2-2-B1-c22-11 | 67 | TN3-2-B1-c22-11 |
| TN2-2-B1-c22-12 | 68 | TN3-2-B1-c22-12 |
| TN2-2-B1-c22-13 | 69 | TN3-2-B1-c22-13 |
| TN2-2-B1-c22-14 | 70 | TN3-2-B1-c22-14 |
| TN2-2-B1-c22-15 | 71 | TN3-2-B1-c22-15 |
| TN2-2-B1-c22-16 | 72 | TN3-2-B1-c22-16 |
| TN2-2-B1-c7 | 73 | TN3-2-B1-c7 |
| TN2-2-B1-C19 | 74 | TN3-2-B1-C19 |
| TN2-2-B1-C1 | 75 | TN3-2-B1-C1 |
| TN2-2-B1-C20 | 76 | TN3-2-B1-C20 |
| TN2-2-B1-C53 | 77 | TN3-2-B1-C53 |
| TN2-2-B1-C29 | 78 | TN3-2-B1-C29 |

Example 2

Production and Purification of TNF Binding Polypeptides

The TNF binding polypeptides of the invention were typically produced and purified using the following methods. From a single colony of BL21-AI containing a plasmid vector containing the encoding sequence of the TNF binding polypeptide, a 6 L culture in 2×TY with 100 µg/mL Amp is grown to A600=0.8 before it is induced with 0.20% L-arabinose and expression is continued for 4 hours.

Cells are harvested and inclusion bodies are recovered. Packed cell pellet from 6 L culture is homogenized in 100 mL 50 mM Tris-HCl pH 8.0, 25 w/v % Sucrose, 1 mM EDTA, (lysis-buffer) by sonication. Then 100 mg lysozyme per 100 mL lysis-buffer is added and mixed before the sample is left for 15 min at R.T. The sample is then sonicated for 2-5 min with mixing in between. 100 mL 0.2 M NaCl, 1 w/v % Deoxycholate, Na salt 1 w/v % Nonidet P40, 20 mM Tris-HCl, pH 7.5, 2 mM EDTA (Detergent-buffer) is added and the sample is mixed and sonified again. Inclusion bodies are recovered by centrifugation for 25 min at 8.000 rpm, 4° C. The supernatant is discarded and the pellet resuspended in 100 mL 0.5 w/v % Triton X-100, 1 mM EDTA, pH 8. Inclusion bodies are recovered by centrifugation for 25 min at 8.000 rpm, 4° C. The Triton X-100 buffer wash is repeated once more. Inclusion bodies are recovered by centrifugation for 5 min at 12.000 rpm, 4° C.

Inclusion bodies are resuspended in 50 mL 6 M guanidine, 50 mM Tris pH 8.0, 50 mM DTT. Solution is buffer changed into 8 M urea, 50 mM Tris pH 8.0, 500 mM NaCl, 5 mM β-merc on a Sephadex G-25 Fine matrix column.

Then the protein is captured on NiNTA IMAC column (NiNTA Agarose from Qiagen) and the column washed with 8 M urea, 50 mM Tris pH 8.0, 500 mM NaCl, 5 mM β-merc. The protein is then eluted in 8 M urea, 50 mM Tris pH 8.0, 500 mM NaCl, 5 mM β-merc, 20 mM EDTA.

Capture eluate from the NiNTA IMAC capture column is used for dilution refolding in 1 L scale. 1 L refolding buffer containing 3 M urea, 50 mM Glycine pH 9.5, 250 mM NaCl, 2 mM CaCl2, 0.3 mM Cystamine is filtered and placed in a 2 L bottle in a cold room at 7° C. A magnetic string bar is added and stirring is set to 250 rpm. The denatured capture eluate protein solution is then dripped into the refolding buffer with a constant flow of 100 µL/min using a peristaltic pump. The final protein concentration when the refolding is stopped is at 250 µg/mL.

Multimers are removed on SP-Sepharose (Amersham) with a gradient (R.T.) from 8 M Urea, 50 mM NaAcetate pH 4.5, 2 mM Tris, 2 mM CaCl2 to 8 M Urea, 50 mM NaAcetate pH 4.5, 2 mM Tris, 2 mM CaCl2, 400 mM NaCl. Then a column is packed with Sephadex G-25 Fine matrix in a total matrix volume of approx. 400 mL and 1 litre of 1 M Urea, 25 mM NaCl, 25 mM Tris, pH 7.0 is used for equilibration at 10 ml/min.

Eluate from the SP-sepharose is applied to the Sephadex G-25 Fine matrix at a flow rate of approx. 8 ml/min. The protein is eluted using 1 M Urea, 25 mM NaCl, 25 mM Tris, pH 7.0 at a flow rate of approx. 8 ml/min. The eluate is pooled and the protein concentration is measured.

Granzyme B is added corresponding to a ratio of 1:250% w/w (mg GrB/mg Trimeric TNF binding polypeptide). Following addition the solution is mixed gently and incubated at 25° C. for 24 hours. Following the digestion solid urea is added to the solution yielding a 8 M urea solution and pH is adjusted to pH 4.5 with 1 M NaAcetate.

The TNF binding polypeptides are polished and concentrated on Source 15S column (Amersham) with a gradient (R.T.) from 8 M Urea, 50 mM NaAcetate pH 4.5, 2 mM Tris, 2 mM CaCl2 to 8 M Urea, 50 mM NaAcetate pH 4.5, 2 mM Tris, 2 mM CaCl$_2$, 1000 mM NaCl. Finally, eluted monomer fractions can be formulated in 25 mM NaAcetate pH 5.0, 50 mM NaCl, 50 mM Sucrose by gel filtration on Sephadex G-25 Fine matrix. The step yield is more that 95% and the protein withstands multiple thaw-freeze cycles without visible or measurable precipitations as followed by A410.

Example 3

Biological Activity of TNF Binding Polypeptides

A selection of the TNF binding polypeptides shown in Table 4, namely TN2-2-B1-C22, TN2-2-B1-C31, TN2-2-B1-C24, TN2-2-B1-C22-7, TN2-2-B1-C22-2, TN2-2-B1-C22-8, TN2-2-B1-C22-12, TN2-2-B1-C22-14, TN2-2-B1-C22-19 and the monomeric TN3-2-B1-C22 and TN3-2-B1-C22-7 (corresponding to TN2-2-B1-C22 and TN2-2-B1-C22-7, respectively), were assayed using the L929 tumor cell line, a murine fibroblast-like cell, by measuring their capability to inhibit the biological activity of TNF. The TNF neutralising activity of the selected clones was compared with commercially available TNF antagonists Remicade (Eternacept), Enbrel (Infliximab) and soluble TNF receptor II (TNF RII/TNFRSF1B, R&D Systems Catalog no. 1089-R2-025/CF).

The TNF inhibition assay was performed according to the following assay protocol: L929 cells (ECACC no.: 85011425) are plated out at $3 \times 10^5$/ml the day before assay set-up. The cells must be allowed to adhere and become confluent before adding the test. Dispense 75 µl volumes of cell suspension into the wells of a flat-bottomed, 96-well microtiter plate (Nunclon; Cat. No.: 167008). Leave one row of eight wells without cells, as a blank for the ELISA reader. Test samples are diluted in culture medium containing 2 µg/ml actinomycin D to give a final culture concentration of 1 µg/ml actinomycin D when added the cells. Dissolve actinomycin D (Sigma) in PBS at 20 µg/ml (warming to 37° C. if necessary) and store at −20° C. in 5 ml (or appropriate) portions. Thaw out human TNF as required and dilute to 4 µg/ml with culture medium—the thawed concentrated solution is stable for up to 2 weeks at 4° C. Make a series of dilutions of the test sample in medium (4-fold is suitable for TNF QC). Then dilute the test sample at the different solutions with human TNF 1:1. For each dilution add triplicate 75 µl volumes to the L929 cells. On each plate include a negative control (i.e. tissue culture medium alone) and a positive control (human TNF with no blocker). After addition of the test samples incubate the microtitre plate at 37° C., 5% CO$_2$ for 16 hr. Cell proliferation is measured using MTT (3-[4,5-dimethyl-thiazol-2-yl]-2,5-di-phenyl-tetrazolium bromide) as part of the CellTiter 96 Non-Radioactive Cell Proliferation Assay Kit (Promega): Thaw the MTS- and the PMS solutions. For the preparation of reagents sufficient for one 96 well plate containing cells cultured in a 150 µl volume 3.0 ml of MTS Solution is removed from the amber reagent bottle using aseptic technique and transferred to a test tube. Add 150 µl of PMS Solution to the 3.0 ml of MTS Solution immediately before addition to the culture plate containing cells. Gently swirl the tube to ensure complete mixing of the combined MTS/PMS solution. Pipet 30 µl of the combined MTS/PMS solution into each well of the 96 well assay plate containing 150 µl of cells in culture medium. Incubate the plate for 1-4 hours at 37° C. in a humidified, 5% CO$_2$ atmosphere. Record the absorbance at 490 nm using an ELISA plate reader.

The results from the above TNF inhibition assay are illustrated in FIGS. 1, 2, 3, 4, 5 and 6. It is clearly seen from FIGS. 1, 3 and 4 that the trimeric clones TN2B1C22, TN2B1C31 and TN2B1C24 (corresponding to monomeric TN3-2-B1-C22, TN3-2-B1-C31 and TN3-2-B1-C24), all have equivalent or better TNF neutralising capabilities as compared to Remicade (Infliximab) and soluble TNF receptor II (RII). In particular it can be seen from FIGS. 1 and 3 that TN2-2-B1-C22 and TN2-2-B1-C31 are superior to Enbrel as well. FIG. 1 shows that the TNF inhibiting capability of the monomeric form of TN2B1C22 (i.e. TN3-2-B1-C22) is equivalent to Remicade. From FIG. 2 it is seen that the monomeric form of TN2B1C22-7 (i.e. TN3-B1-C22-7) is superior to Remicade.

Example 4

HUVEC Assay

Human umbilical cord endothelial cells (HUVEC) are primary non transformed human cells that have been isolated from the umbilical cord. The cells can be kept in culture for a few passages. Umbilical cord endothelial cells are sensitive for TNF. After activation of the cells by TNF, the cells start producing inflammatory cytokines like IL8 and IL6. These responses represent the first line of defence after a bacterial infection. To investigate the efficacy of the TNF binding polypeptides we tested the inhibition of TNF induced IL6 and IL8 production.

HUVEC cells (Cambrex Lot. Nr. 2f1828) are plated out the day before assay set-up in EGM-2 medium. The cells must be allowed to adhere and become confluent before the test. Per well 200 μl of a $5\times10^4$/mL HUVEC cell suspension is pipetted into the wells of a flat-bottomed, 96-well microtiter plate (Nunclon; Cat. No.: 167008). Test samples are diluted in culture medium. The test samples are prepared as follows: TNF binding polypeptides, Enbrel or Remicade at indicated concentrations are incubated for 15 min. with 3 ng/ml human TNF and then 100 μl of the solutions is added to the HUVEC cells, giving a final concentration of 1 ng/ml TNF. The exact range of dilutions depends upon the nature of the test sample and the sensitivity of the target. Each plate includes a negative control (i.e. tissue culture medium alone) and a positive control. After addition of the test samples the microtiter plate is incubated at 37° C., 5% $CO_2$ for 16-24 hr.

The next day supernatant is harvested from the wells and IL6 and IL8 (10× diluted) Elisa is performed to measure the TNF induced cytokines according to the protocol of Human IL-6 & IL-8-ELISA (96 well maxisorp Nunc plate). The following materials are used for the ELISA: Human recombinant IL-6: Cat. No.: 206-IL-010 (R&D Systems), Monoclonal anti-human IL-6 antibody Code no.: MAB 206 (R&D Systems), Biotinylated anti-human IL-6 antibody Cat. No.: BAF206 (R&D Systems), Human recombinant IL-8: Cat. No.: 208-IL (R&D Systems), Monoclonal anti-human IL-8 antibody Code no.: MAB208 (R&D Systems), Biotinylated anti-human IL-8 antibody Cat. No.: BAF208 (R&D Systems).

The TNF binding polypeptides TN3-2-B1-C31, TN3-2-B1-C22-7, TN3-2-B1-C22-8 were tested in the above HUVEC assay. The results from this experiment are illustrated in FIGS. 6 and 7. As can be seen from these figures, the TNF binding polypeptides TN3-2-B1-C31, TN3-2-B1-C22-7, TN3-2-B1-C22-8 are perfectly able to block the induction of IL8 (FIG. 6) and IL6 (FIG. 7). The TNF binding polypeptides TN3-2-B1-C22-7 (C22-7) and TN3-2-B1-C22-8 (C22-8) are as good as Enbrel and significantly better than Remicade in this task.

Example 5

Pegylated TNF Binding Polypeptide GG-I10-TN-2-B1-C22-7

The trimeric TNF binding polypeptide GG-I10-TN-2-B1-C22-7 (SEQ ID NO:79) was prepared essentially as described in Example 2, with the exemption that the solution was buffer changed into the below mentioned pegylation buffer on a Sephadex G-25 Fine matrix column.

This construct had been adopted for pegylation by the deletion of the first nine amino acids in the sequence, and the addition of two glycine residues at the N-terminus. A 0.5 mg/mL solution of GG-I10-TN-2-B1-C22-7 in 8 M Urea, 50 mM $NaH_2PO_4$ pH 6.0, 50 mM NaCl containing 20 mM $NaCNBH_3$ was added a 10 molar excess of methoxy poly(ethylene glycol)-Butyr-aldehyde (mPEG-ALD) with an average Mw of 20 kDa. The reaction was stirred over night at approximately 20° C. Following, the extent of reaction between protein and the mPEG-ALD was determined by SDS-PAGE.

To separate the pegylated GG-I10-TN-2-B1-C22-7 from un-reacted monomers a cation exchange column was run. A 1 mL Source 15S column (Amersham) equilibrated in 8 M Urea, 50 mM NaAcetate pH 4.5, 2 mM $CaCl_2$ was loaded with the reaction mixture and a linear gradient from 8 M Urea, 50 mM NaAcetate pH 4.5, 2 mM $CaCl_2$ to 8 M Urea, 50 mM NaAcetate pH 4.5, 2 mM $CaCl_2$, 1000 mM NaCl was used to fractionate pegylated from non-pegylated protein.

The L929 assay was performed as described in Example 3 using pegylated GG-I10-TN-2-B1-C22-7 (20KPEG-GG-I10-TN-2-B1-C22-7), non-pegylated GG-I10-TN-2-B1-C22-7 (GG C22-7), and un-mutated TN-2-B1-C22-7 (C22-7) (SEQ ID NO:32). Enbrel and Remicade were used as controls.

As can be seen from FIG. 8 the efficacy of the pegylated material in in-vitro assays was not significantly different from the non-pegylated material.

Example 6

In-Vivo Blocking of Inflammatory Cytokine Induction in Mice

Mice were injected with the TNF binding polypeptide TN2-2-B1-C31 at 3 different concentrations: 12.5, 25 and 50 μg per mouse. After 30 minutes the mice were injected intravenously with 3 μg of human TNF. Normally as seen in the controls, human TNF induces inflammatory cytokine production such as IL-6 and MCP-1. However, as can be seen from FIGS. 9 and 10, the TNF binding polypeptide TN2-2-B1-C31 is able to block the induction of these inflammatory cytokines.

Example 7

In Vivo Prevention of Rheumatoid Arthritis Induction

The Tg197 transgenic mice line expresses human TNF. The mice carry 5 copies of human TNF and develop polyarthritis at 3 to 4 weeks of age. The disease is clinically detectable at week 4 with swelling and deformation of the ankle joints. This leads to severe joint destruction and impairment of leg movement of the hind legs at 8 to 10 weeks of age. Progressive weight loss is common. The appropriate administration of TNF neutralizing agents prevents the development of the disease. In order to test the efficacy of the TNF binding polypeptides of the invention in the prevention of polyarthritis in the Tg197 murine arthritis model, TN-2-B1-C31 was administered to groups of Tg197 mice that are matched in age and weight. The treatment was started prophylactic at 3-4 weeks of age. The TNF binding polypeptides were administered at three dosages: 3.3, 1.0, and 0.5 mg/kg three times weekly intra peritoneal (i.p.) for 5 weeks. A blood sample was taken before the second i.p. injection and by the end of the study.

The severity of arthritis was evaluated and expressed in arthritic scores ranging from AS-0 to AS-3 where 0 is no arthritis and 3 is completely lamed due to cartilage degradation and bone degradation in the joints.

Figure 11:
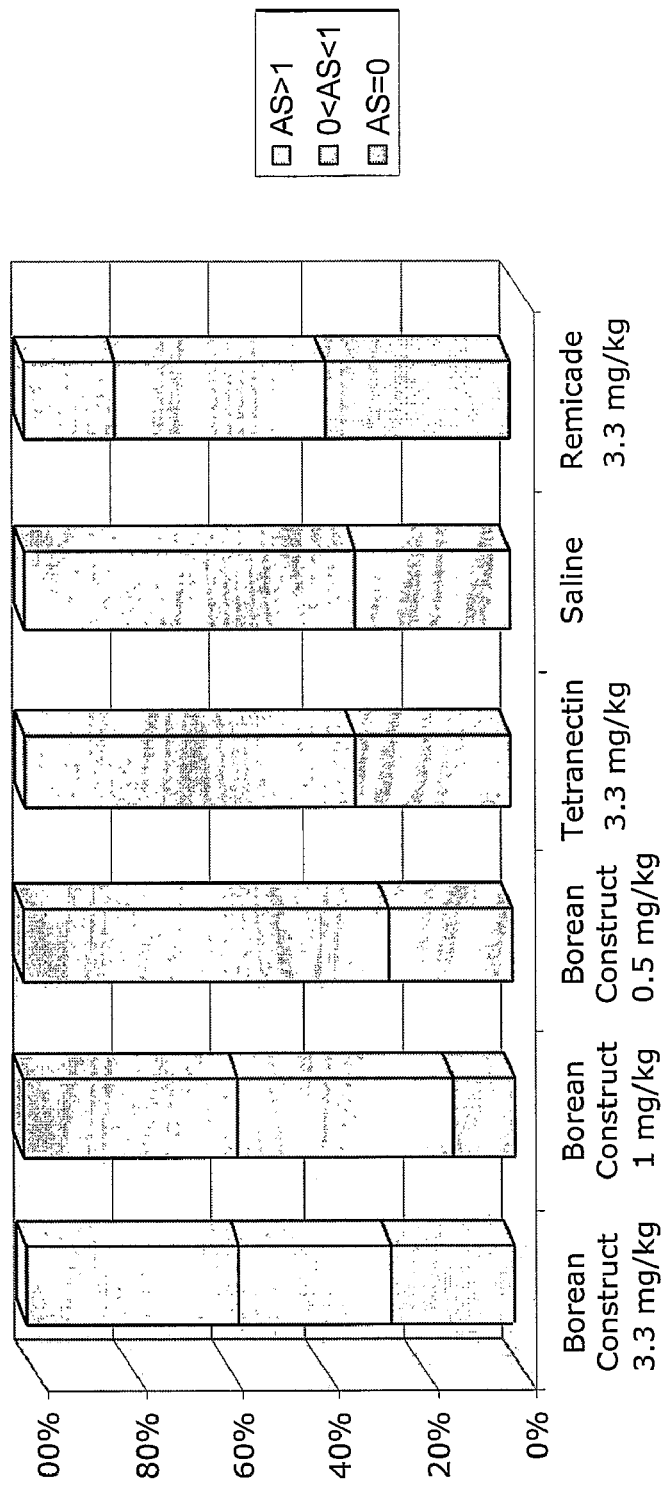
FIG. 11 shows the arthritic score for different groups of mice treated with TN2-2-B1-C31 (termed "Borean construct" in the figure) at 3 different doses, a saline solution (negative control), wild type Tetranectin (negative control) and Remicade (positive control).

FIG. 11 shows the arthritic score for the different groups of mice treated with TN2-2-B1-C31 (termed "Borean construct" in the figure) at 3 different doses, a saline solution (negative control), wild type Tetranectin (negative control) and Remicade (positive control). As can be seen in FIG. 11, the higher the dose of TN2-2-B1-C31 the lower the arthritic score. This shows that TN2-2-B1-C31 is effective in the treatment of rheumatoid arthritis.

The invention claimed is:

1. An isolated polypeptide capable of binding tumour necrosis factor (TNF), where said polypeptide comprises the amino acid sequence KRWSRYF (SEQ ID NO: 1).

2. A polypeptide according to claim 1, wherein said amino acid sequence forms part of a C-type lectin-like domain.

3. A polypeptide according to claim 2, wherein the C-type lectin-like domain is from tetranectin.

4. A polypeptide according to claim 3, wherein the C-type lectin-like is an amino acid sequence comprising residues 50-181 in SEQ ID NO:79.

5. A polypeptide according to claim 4, wherein the aspartic acid residue no. 165 in SEQ ID NO:79 is mutated to glycine.

6. A polypeptide according to claim 1, further comprising the amino acid sequence $PX_1PX_2N$ (SEQ ID NO:2), wherein $X_1$ and $X_2$ are each independently amino acid residues.

7. A polypeptide according to claim 1, further comprising the amino acid sequence $X_1PX_2PX_3NX_4$ (SEQ ID NO:3) wherein $X_1$ is a hydrophilic amino acid selected from the group consisting of S, T, N, Q, E, D, K, R and H; $X_2$ and $X_3$ are each independently amino acid residues, and $X_4$ is a hydrophobic amino acid selected from the group consisting of M, A, V, L, P, W, F, Y and C.

8. A polypeptide according to claim 1, further comprising the amino acid sequence $X_1PX_2PX_3NX_4$ (SEQ ID NO:3), wherein $X_1$ is a hydrophilic amino acid selected from the group consisting of S, T, N, Q, E, D, K, R and H; $X_2$ and $X_3$ are each independently amino acid residues, and $X_4$ is an aromatic amino acid selected from the group consisting of W, F and Y.

9. A polypeptide according to claim 1, further comprising an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27 and SEQ ID NO:28.

10. A polypeptide according to claim 9, selected from the group consisting of TN3-2-B1-C22 (SEQ ID NO:29), TN3-2-B1-C31(SEQ ID NO:30), TN3-2-B1-C24(SEQ ID NO:31), TN3-2-B1-C22-7 (SEQ ID NO:32), TN3-2-B1-c22-1(SEQ ID NO:33), TN3-2-B1-c22-2 (SEQ ID NO:34), TN3-2-131-c22-3 (SEQ ID NO:35), TN3-2-B1-c22-4 (SEQ ID NO:36), TN3-2-B1-c22-6 (SEQ ID NO:37), TN3-2-B1-c22-7 (SEQ ID NO:38), TN3-2-B1-c22-8 (SEQ ID NO:39), TN3-2-B1-c22-9 (SEQ ID NO:40), TN3-2-B1-c22-10 (SEQ ID NO:41), TN3-2-B1c22-11 (SEQ ID NO:42), TN3-2-B1-c22-12 (SEQ ID NO:43), TN3-2-B1-c22-13 (SEQ ID NO:44), TN3-2-B1-c22-14 (SEQ ID NO:45), TN3-2-B1-c22-15 (SEQ ID NO:46), TN3-2-B1- c22-16 (SEQ ID NO:47), TN3-2-B1-c7 (SEQ ID NO:48), TN3-2-B1-C19 (SEQ ID NO:49), TN3-2-B1-C1 (SEQ ID NO:50), TN3-2-B1-C20 (SEQ ID NO:51), TN3-2-B1-053 (SEQ ID NO:52) and TN3-2-B1-C29 (SEQ ID NO:53).

11. A polypeptide according to claim 3, wherein said C-type lectin-like domain is linked to a trimerising domain derived from tetranectin.

12. A polypeptide according to claim 11, wherein the trimerising domain derived from tetranectin comprises a sequence having at least 68% amino acid sequence identity with the sequence of SEQ ID NO:80.

13. A polypeptide according to claim 12, wherein the amino acid sequence identity is at least 75%.

14. A polypeptide according to claim 11, wherein the trimerising domain derived from tetranectin comprises the amino acid sequence SEQ ID NO:81.

15. A polypeptide according to claim 11, selected from the group consisting of TN2-2-B1-C22 (SEQ ID NO:54), TN2-2-B1-C31 (SEQ ID NO:55), TN2-2-B1-C24 (SEQ ID NO:56), TN2-2-B1-C22-7 (SEQ ID NO:57), TN2-2-B1-c22-1 (SEQ ID NO:58), TN2-2-B1-c22-2 (SEQ ID NO:59), TN2-2-B1-c22-3 (SEQ ID NO:60), TN2-2-B1-c22-4 (SEQ ID NO:61), TN2-2-B1-c22-6 (SEQ ID NO:62), TN2-2-B1-c22-7 (SEQ ID NO:63), TN2-2-B1-c22-8 (SEQ ID NO:64), TN2-2-B1-c22-9(SEQ ID NO:65), TN2-2-B1-c22-10 (SEQ ID NO:66), TN2-2-B1-c22-11 (SEQ ID NO:67), TN2-2-B1-c22-12 (SEQ ID NO:68), TN2-2-B1-c22-13 (SEQ ID NO:69), TN2-2-B1-c22-14 (SEQ ID NO:70), TN2-2-B1-c22-15 (SEQ ID NO:71), TN2-2-B1-c22-16 (SEQ ID NO:72), TN2-2-B1-c7 (SEQ ID NO:73), TN2-2-B1-C19 (SEQ ID NO:74), TN2-2-B1-C1 (SEQ ID NO:75), TN2-2-B1-C20 (SEQ ID NO:76), TN2-2-B1-053 (SEQ ID NO:77), TN2-2-B1-C29 (SEQ ID NO:78) and GG-110-TN-2-B1-C22-7(SEQ ID NO:79).

16. An isolated nucleic acid which comprises a sequence encoding a polypeptide as defined in claim 1.

17. An expression vector comprising the isolated nucleic acid of claim 16.

18. A host cell comprising the expression vector of claim 17.

19. A method for the preparation of a polypeptide capable of binding TNF as defined in claim 1, said method comprising the steps of (i) expressing the isolated nucleic acid of claim 16 under such conditions that said polypeptide is expressed, and (ii) recovering the polypeptide.

20. A pharmaceutical composition comprising the polypeptide according to claim 1 and a pharmaceutically acceptable excipient.

21. A method of treating a subject having rheumatoid arthritis, psoriasis or Crohn's disease, comprising administering to said subject an effective amount of the polypeptide according to claim 1.

22. An assay method for detecting TNF in a sample comprising (i) contacting said sample with a polypeptide according to claim 1, and (ii) detecting the binding of TNF to said polypeptide.

23. A method of treating rheumatoid arthritis, psoriasis, or inflammatory bowel disease comprising administering to a subject in need thereof an effective amount of the polypeptide of claim 1.

24. A method of preparing a pharmaceutical preparation comprising combining the polypeptide of claim 1 with at least one of pharmaceutically acceptable excipient, a pharmaceutically acceptable carrier, a pharmaceutically acceptable buffer or a pharmaceutically acceptable stabilizer.

25. A method of treating a subject having rheumatoid arthritis, psoriasis, or inflammatory bowel disease, comprising administering to said subject an effective amount of the composition according to claim 20.

26. A polypeptide according to claim 12, wherein the amino acid sequence identity is at least 87%.

27. A polypeptide according to claim 12, wherein the amino acid sequence identity is at least 92%.

* * * * *